US009371326B2

(12) United States Patent
Hong et al.

(10) Patent No.: US 9,371,326 B2
(45) Date of Patent: *Jun. 21, 2016

(54) METHOD FOR SYNTHESIZING SAPROPTERIN DIHYDROCHLORIDE

(71) Applicants: ASYMCHEM LABORATORIES (TIANJIN) CO., LTD, TEDA Tianjin (CN); ASYMCHEM LIFE SCIENCE (TIANJIN) CO., LTD, TEDA Tianjin (CN); TIANJIN ASYMCHEM PHARMACEUTICAL CO., LTD, Teda Tianjin (CN); ASYMCHEM LABORATORIES (FUXIN) CO., LTD, Liaoning (CN); JILIN ASYMCHEM LABORATORIES CO.,LTD, Jilin (CN)

(72) Inventors: Hao Hong, Tianjin (CN); James Gage, Tianjin (CN); Chaoyong Chen, Tianjin (CN); Jiangping Lu, Tianjin (CN); Yan Zhou, Tianjin (CN); Shuangyong Liu, Tianjin (CN)

(73) Assignees: ASYMCHEM LABORATORIES (TIANJIN) CO., LTD (CN); ASYMCHEM LIFE SCIENCE (TIANJIN) CO., LTD (CN); TIANJIN ASYMCHEM PHARMACEUTICAL CO., LTD (CN); ASYMCHEM LABORATORIES (FUXIN) CO., LTD (CN); JILIN ASYMCHEM LABORATORIES CO., LTD (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/394,079

(22) PCT Filed: Dec. 27, 2012

(86) PCT No.: PCT/CN2012/087732

§ 371 (c)(1),
(2) Date: Dec. 17, 2014

(87) PCT Pub. No.: WO2013/152608

PCT Pub. Date: Oct. 17, 2013

(65) Prior Publication Data

US 2015/0119573 A1 Apr. 30, 2015

(30) Foreign Application Priority Data

Apr. 10, 2012 (CN) .......................... 2012 1 0102879

(51) Int. Cl.
| C07D 475/04 | (2006.01) |
|---|---|
| C07D 239/50 | (2006.01) |
| C07D 239/48 | (2006.01) |
| C07D 239/47 | (2006.01) |
| C07D 303/48 | (2006.01) |
| C07D 317/26 | (2006.01) |
| C07D 317/28 | (2006.01) |
| C07D 317/32 | (2006.01) |
| C07C 209/62 | (2006.01) |
| C07C 221/00 | (2006.01) |
| C07C 225/06 | (2006.01) |

(52) U.S. Cl.
CPC ............ *C07D 475/04* (2013.01); *C07C 209/62* (2013.01); *C07C 221/00* (2013.01); *C07C 225/06* (2013.01); *C07D 239/50* (2013.01); *C07D 303/48* (2013.01); *C07D 317/26* (2013.01); *C07D 317/28* (2013.01); *C07D 317/32* (2013.01)

(58) Field of Classification Search
CPC .. C07D 475/04; C07D 239/50; C07D 239/48; C07D 239/47; C07D 303/48; C07D 317/26; C07D 317/28; C07D 317/32; C07C 209/62; C07C 221/00; C07C 225/06
USPC .......................................... 544/258
See application file for complete search history.

(56) References Cited

U.S. PATENT DOCUMENTS

| 2006/0142573 A1 | 6/2006 | Tazawa | |
|---|---|---|---|
| 2015/0105555 A1* | 4/2015 | Hong et al. | .................. 544/258 |

FOREIGN PATENT DOCUMENTS

| CN | 102627644 A | 8/2012 |
|---|---|---|
| CN | 102633799 A | 8/2012 |
| EP | 0153696 A2 | 2/1985 |
| EP | 0191335 A2 | 8/1986 |
| JP | 574990 A | 1/1982 |
| JP | 60204786 A | 10/1985 |
| WO | 2005063752 A1 | 12/2003 |
| WO | 2009088979 A1 | 7/2009 |

OTHER PUBLICATIONS

International Search Report for corresponding application PCT/CN2012/087737 filed Dec. 27, 2012; Mail date Apr. 4, 2013.
International Search Report PCT/CN2012/087732 filed Dec. 27, 2012; Mail date Apr. 4, 2013.

* cited by examiner

*Primary Examiner* — Venkataraman Balasubramanian
(74) *Attorney, Agent, or Firm* — Cantor Colburn LLP

(57) ABSTRACT

Disclosed is a method for synthesizing sapropterin dihydrochloride. The present disclosure reduces a synthesis route of the sapropterin dihydrochloride, and resolves a racemate intermediate or an intermediate having a low antimer isomerism value by using a chiral resolving reagent, thereby obtaining an intermediate having a high antimer isomerism value. Raw materials are cheap and readily available, and the cost is significantly reduced, hence providing an effective scheme for mass industrial production of the sapropterin dihydrochloride.

9 Claims, 1 Drawing Sheet

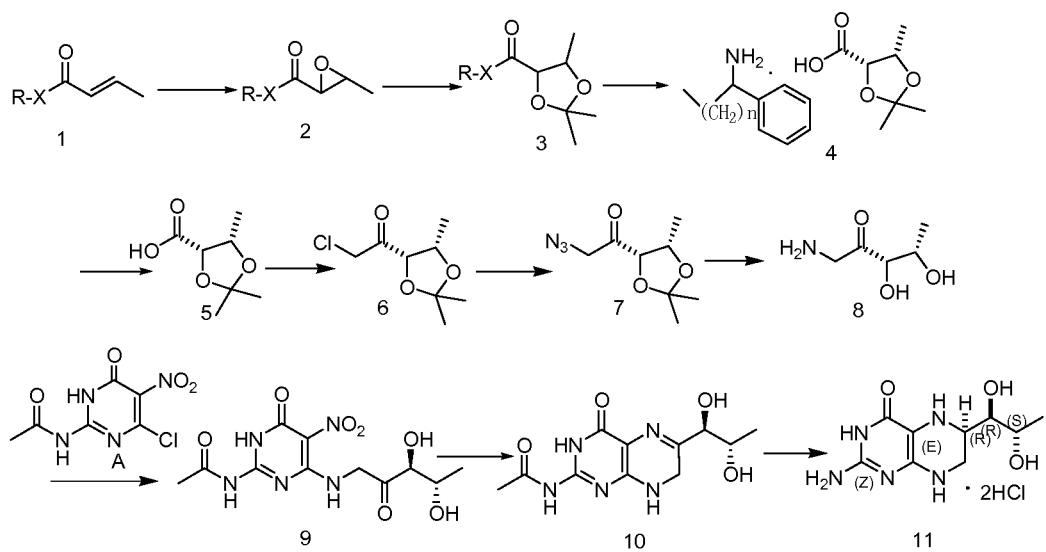

METHOD FOR SYNTHESIZING SAPROPTERIN DIHYDROCHLORIDE

TECHNICAL FIELD

The present disclosure relates to a method for synthesizing a medicine for treating Phenylketonuria (PKU), and particularly to a method for synthesizing sapropterin dihydrochloride.

BACKGROUND

Sapropterin dihydrochloride, chemical name (6R)-2-amino-6-[(1R,2S)-1,2-dihydroxypropyl]-5,6,7,8-tetrahydro-4(1H)-pteridinone dihydrochloride, molecular formula $C_9H_{15}N_5O_3 \cdot 2HCl$, and CAS registry number 69056-38-28, is a synthetic product of tetrahydrobiopterin ($BH_4$) dihydrochloride. BH4 is a cofactor of Phenylalanine Hydroxylase (PAH). Tyrosine is acquired from Phenylalanine (Phe) through hydroxylation under the action of PAH which is low in activity or even inactive in PKU patients, while $BH_4$ is able to activate PAH, promote normal oxidative metabolism of Phe in the bodies of the patients, and reduce the Phe levels in the bodies of some patients. On Dec. 16, 2007, the sapropterin dihydrochloride tablets produced by BioMarin Pharmaceutical Inc. in USA were approved by the Food and Drug Administration (FDA) for marketing for treatment of PKU. Because of the effective activity of sapropterin dihydrochloride, it is extremely necessary to select a route applicable to industrial production with high product purity.

At present, $BH_4$ is mainly synthesized by the following methods reported in literatures:
1. Preparation using 4-hydroxy-2,5,6-triaminopyrimidine (ATP) and 5-deoxy-L-arabinose as raw materials, please see literature E. L. Patterson et al., J. Am. Chem. Soc. 78, 5868 (1956).
2. Preparation using TAP and 5-deoxy-L-arabinose phenylhydrazone as raw materials, please see literature Matsuura et al., Bull. Chem. Soc. Jpn., 48,3767 (1975);
3. Preparation by reaction of raw materials hydroxyl-protected TAP and 4-acetyl-2,3-epoxypentanal through oxidation of iodine and a dehydroxylation protecting group, please see literature Matsuura et al., Chemistry of Organic Synthesis, Ml/g. 46. No. 6, P 570 (1988).

These traditional methods for preparing BH4 have the following major disadvantages: raw materials are expensive, arabinose which can be hardly acquired is used as a carbon atom radical for asymmetric synthesis; there are multiple steps in reactions with low yield, and low product purity, 5-deoxy-L-arabinose is easily degraded in a reaction solution, and products of the synthesis routes above have low stereoselectivity. To sum up, the traditional synthesis methods are not applicable to mass industrial production. Therefore, a synthesis route, which is applicable to industrial production with high product purity, high yield and high stereoselectivity, needs to be searched urgently.

SUMMARY

The present disclosure provides a method for synthesizing a sapropterin dihydrochloride compound. The present disclosure reduces a synthesis route of sapropterin dihydrochloride, and resolves a racemate intermediate or an intermediate having a low antimer isomerism value by using a chiral resolving reagent, thereby obtaining an intermediate having a high antimer isomerism value. Raw materials are cheap and readily available, and the cost is significantly reduced, hence providing an effective scheme for mass industrial production of sapropterin dihydrochloride.

A technical solution of the present disclosure: a method for synthesizing sapropterin dihydrochloride, wherein it includes the following specific steps:

Step 1: in the presence of a polar solvent, add compound 1

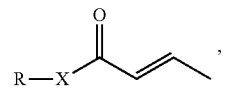

where X=NH or O, R=C1 to C6 alkane or benzyl, increase the system temperature to 35° C. to 50° C., add an oxidant, react for 2 to 5 hours while preserving the temperature, then add a strong base aqueous solution having a concentration of 10% to 20% to the system, while preserving the temperature, react the system for 3 to 4 hours after adding the strong base aqueous solution, and perform extraction and concentration to obtain compound 2 having a structural formula of

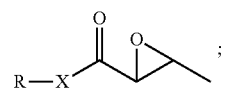

when X is NH, compound 1 is alkyl crotonamide or benzamide, and compound 2 is 2,3 epoxy-alkylamide butyrate; when X is oxygen, compound 1 is alkyl crotonate or benzyl crotonate and compound 2 is 2,3 epoxy-alkylbutyrate or 2,3 epoxy-benzyl butyrate;

wherein ratio of the use amount of

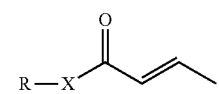

to that of the polar solvent is 1 g/5 to 20 ml, the molar ratio of

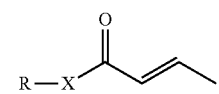

to the oxidant is 1:1 to 3, and the molar ratio of

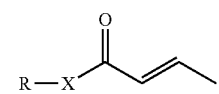

to the strong base is 1:1 to 3; Step 1 can be also performed according to a method of patent 200910070240.8;

Step 2: add a Lewis acid in the presence of acetone, control the temperature at 10° C. to 30° C., add compound 2, react for 5 to 10 hours while preserving the temperature, add an inorganic base solution having a concentration of 5% to 10% to the system, and perform liquid separation, extraction and concentration to the system to obtain compound 3 having a structural formula of

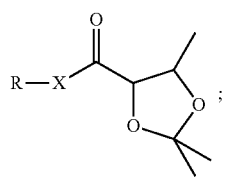

when X is NH, compound 3 is 2,3-acetonide-alkylbutyramide or 2,3-acetonide-benzylbutyramide; when X is oxygen, compound 3 is 2,3-acetonide-alkylbutyrate or 2,3-acetonide-benzyl butyrate;

wherein the molar ratio of compound 2 to acetone is 1:3 to 15; the molar ratio of compound 2 to the Lewis acid is 1:0.1 to 1; and the molar ratio of compound 2 to the inorganic base is 1:0.5 to 3;

Step 3: add compound 3 in the presence of a polar solvent, increase the temperature to 25° C. to 40° C., add pure water and an alkaline solution, react for 3 to 8 hours while preserving the temperature, perform centrifugation, dissolve a filter cake in a polar solvent which is the same as the polar solvent used in the reaction, add a resolving reagent, preserve the temperature at 15° C. to 30° C. for 3 to 5 hours, perform centrifugation and drying to obtain compound 4, i.e. 1-phenylalkylamine (4S,5S)-2,2,5-trimethyl-1,3-dioxolane-4-carboxylate having a structural formula of

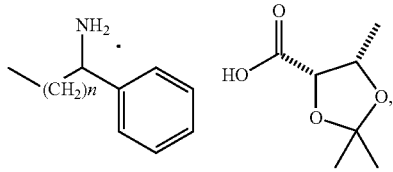

where n=0, 1; wherein the ratio of the use amount of compound 3 to that of the polar solvent used in the reaction is 1 g/3 to 10 ml; the molar ratio of compound 3 to pure water is 1:0.5 to 3; the molar ratio of compound 3 to an alkaline substance in the alkaline solution is 1:0.5 to 2; the ratio of the use amount of compound 3 to that of the polar solvent for dissolving the filter cake is 1 g/2 to 10 ml; the molar ratio of compound 3 to the resolving reagent is 1:1 to 5;

Step 4: add compound 4 in the presence of an ether solvent, then add an inorganic acid aqueous solution having a concentration of 5% to 10% to the system to regulate the pH to 1 to 3, control the temperature at −10° C. to 10° C., preserve the temperature for 1 hour, perform liquid separation to obtain an organic phase, add N,N-diisopropylethylamine to the organic phase, and concentrate the system to obtain compound 5, i.e. (4S,5S)-2,2,5-trimethyl-1,3-dioxolan-4-methanoic acid having a structural formula of

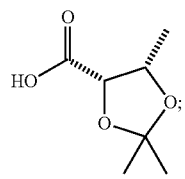

wherein the ratio of the use amount of compound 4 to that of the ether solvent is 1 g/3 to 10 ml and the molar ratio of compound 4 to N,N-diisopropylethylamine is 1:0.8 to 3;

Step 5: add compound 5 and N,N-diisopropylethylamine in the presence of an ether solvent, reduce the temperature to −30° C. to 0° C., add a chloroformate, react for 1 to 2 hours while preserving the temperature, introduce a diazomethane gas for 1 to 2 hours, add a hydrochloride ethanol solution, react for 1 to 2 hours, add an alkaline reagent to regulate the pH value to 7 to 9, perform extraction, liquid separation and concentration to obtain compound 6, i.e. (4S,5S)-2,2,5-trimethyl-5-chloroacetyl-1,3-dioxolane having a structural formula of

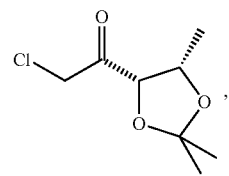

wherein the ratio of the use amount of compound 5 to that of the ether solvent is 1 g/5 to 15 ml; the molar ratio of compound 5 to N,N-diisopropylethylamine is 1:1 to 5; the molar ratio of compound 5 to the chloroformate is 1:1 to 3; and the molar ratio of compound 5 to hydrogen chloride in the hydrochloride ethanol solution is 1:1 to 5;

Step 6: add compound 6, a trinitride and a catalyst in the presence of a polar solvent, react the system at 15° C. to 40° C. for 20 to 30 hours while preserving the temperature, then perform filtering and concentration to obtain a solution of compound 7 which is used directly in the next step; compound 7 is (4S,5S)-2,2,5-trimethyl-5-(2-azidoacetyl)-1,3-dioxolane having a structural formula of

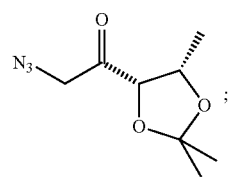

wherein the ratio of the use amount of compound 6 to that of the polar solvent is 1 g/5 to 15 ml; the molar ratio of compound 6 to the trinitride is 1:1 to 4; and the molar ratio of compound 6 to the catalyst is 1:0.05 to 0.8;

Step 7: add triphenylphosphine and water, or palladium on carbon and hydrogen, or Raney nickel and hydrogen in the presence of an ether solvent, regulate the pH of the system to 1 to 4 with an acid reagent, add a solution of compound 7, preserve the temperature at 10° C. to 30° C., react for 5 to 10 hours, perform suction filtration and concentration to obtain a filtrate containing compound 8, the filtrate being used directly in the next step or a solid of compound 8 being separated from the filtrate for use in the next step; the compound 8 is (3S, 4S)-1-amino-3,4-dihydroxy-2-pentanone having a structural formula of

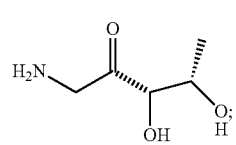

wherein the ratio of the use amount of compound 7 to that of the ether solvent is 1 g/5 to 15 ml; the molar ratio of compound 7 to triphenylphosphine is 1:0.1 to 3; the ratio of the use amount of compound 7 to that of water is 1:0.1 to 3; the mass ratio of compound 7 to 5% palladium on carbon or 10% palladium on carbon or Raney nickel is 1:0.05 to 0.6; introduce hydrogen until the pressure of the system is 0.4 to 0.9 MPa;

Step 8: add a catalyst, compound A, i.e. 2-amino-6-chloro-5-nitro-3H-pyrimidin-4-one having a structural formula of

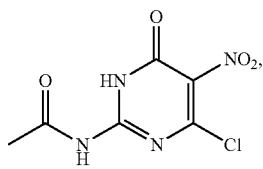

compound 8, and an alkaline reagent in the presence of an alcoholic solvent and pure water, react the system at 30° C. to 80° C. for 4 to 8 hours while preserving the temperature, add a buffer solution to regulate the pH of the system to 6 to 8, and filter the system to obtain compound 9, i.e. 2-acetylamino-5-nitro-6-((3S,4S)-3,3-dihydroxy-2-oxo-pentylamino)-pyrimidin-4-one having a structural formula of

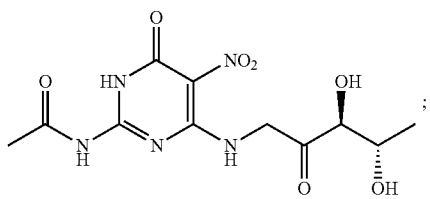 [SMILES: CC(=O)Nc1nc(NCC(=O)[C@@H](O)[C@H](C)O)c([N+](=O)[O-])c(=O)[nH]1]

wherein the ratio of the use amount of compound 8 to that of the alcoholic solvent is 1 g/5 to 15 ml; the ratio of the use amount of compound 8 to that of pure water is 1 g/1 to 5 ml; the molar ratio of compound 8 to compound A is 1:1 to 1.5; the molar ratio of compound 8 to the catalyst is 1:0.05 to 0.5; and the molar ratio of compound 8 to the alkaline reagent is 1:3 to 8;

Step 9: add a catalyst in the presence of compound 9 and a polar solvent, introduce hydrogen until the pressure of the system is 0.4 to 0.9 MPa, control the temperature of the system at 15° C. to 30° C. and the pressure at 0.4 to 0.9 MPa, react for 18 to 24 hours, filter the system, and regulate the pH of the system to 11 to 12 with an alkaline reagent to obtain a solution of compound 10 to be used directly in the next step, compound 10 is acetylamino-7,8-dihydropteridine having a structural formula of

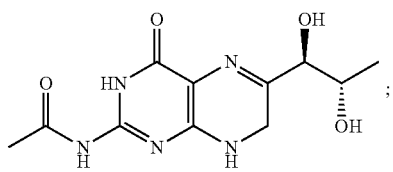 [SMILES: CC(=O)Nc1nc2c(c(=O)[nH]1)N=C([C@@H](O)[C@H](C)O)CN2]

wherein the ratio of the use amount of compound 9 to that of the polar solvent is 1 g/20 to 50 ml and the mass ratio of compound 9 to the catalyst is 1:0.05 to 0.6;

Step 10: add a catalyst in the presence of the solution of the compound 10 obtained in Step 9, introduce hydrogen until the pressure of the system is 0.4 to 0.9 MPa, control the temperature of the system at 10° C. to 30° C., control the pressure at 0.4 to 0.9 MPa, react for 72 to 84 hours, perform quenching in dilute hydrochloric acid having a concentration of 10% to 20% after reacting thoroughly, and perform suction filtration and drying to the system to obtain compound 11, i.e. a target product, a sapropterin dihydrochloride crude product, and further crystallize and purify the sapropterin dihydrochloride crude product with an alcoholic solvent or a ketone solvent at 0° C. to 40° C. to obtain a sapropterin dihydrochloride pure product, wherein the mass ratio of compound 10 to the catalyst is 1:0.05 to 0.6; the molar ratio of compound 10 to hydrochloric acid is 1:3 to 10; and the ratio of the use amount of compound 10 to that of the alcoholic solvent or the ketone solvent is 1 g/5 to 25 ml.

The solar solvent in Step 1 is water, methanol, ethanol or isopropanol, preferably water, methanol or ethanol, optimally water; the oxidant is N-bromobutanimide, meta-chloroperoxybenzoic acid, hydrogen peroxide having a concentration of 35% or a toluene solution of tert-butyl hydroperoxide having a concentration of 50%, preferably N-bromobutanimide, meta-chloroperoxybenzoic acid or a toluene solution of tert-butyl hydroperoxide having a concentration of 50%, and optimally N-bromobutanimide; the strong base is sodium hydroxide or potassium hydroxide, preferably sodium hydroxide;

the ratio of the use amount of

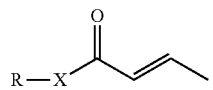

to that of the polar solvent is 1 g/5 to 15 ml, preferably 1 g/6 to 12 ml; the molar ratio of

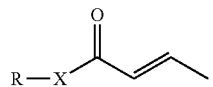

to the oxidant is 1:1 to 2.5, preferably 1:1 to 2; the molar ratio of

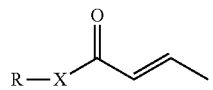

to the strong base is 1:1 to 2.5, preferably 1:1 to 2.

In Step 2, the Lewis acid is aluminium chloride, ferric chloride, zinc chloride, a boron trifluoride diethyl etherate solution having a concentration of 47%, zinc bromide, or lithium chloride, preferably aluminium chloride, boron trifluoride diethyl etherate solution, having a concentration of 47%, zinc bromide or lithium chloride, and optimally aluminium chloride; the inorganic base is sodium bicarbonate, sodium carbonate, sodium hydroxide, potassium hydroxide, potassium carbonate or potassium bicarbonate, preferably sodium bicarbonate, sodium carbonate, potassium carbonate or potassium bicarbonate, optimally sodium carbonate;

the ratio of the use amount of compound 2 to that of acetone is 1:5 to 15, preferably 1:5 to 10; the molar ratio of compound 2 to the Lewis acid is 1:0.1 to 0.8, preferably 1:0.1 to 0.6; the ratio of the use amount of compound 2 to that of the inorganic base is 1:0.5 to 2.5, preferably 1:0.5 to 1.5.

In Step 3, the polar solvent is tetrahydrofuran, methanol or ethanol, preferably tetrahydrofuran or methanol, optimally methanol; the resolving reagent is L-α-phenylethylamine or L-α-amphetamine, preferably L-α-phenylethylamine; the alkaline solution is a methanol solution of sodium methoxide having a concentration of 29%, a potassium hydroxide aqueous solution having a concentration of 20% or a sodium hydroxide aqueous solution having a concentration of 20%, preferably the methanol solution of sodium methoxide having a concentration of 29% or the potassium hydroxide aqueous solution having a concentration of 20%, optimally the methanol solution of sodium methoxide having a concentration of 29%;

the ratio of the use amount of compound 3 to that of the polar solvent used in the reaction is 1 g/3 to 8 ml, preferably 1 g/4 to 8 ml; the molar ratio of compound 3 to pure water is 1:0.5 to 1.8, preferably 1:0.5 to 1.5; the molar ratio of compound 3 to the alkaline substance in the alkaline solution is 1:0.5 to 1.8, preferably 1:0.5 to 1.5; the ratio of the use amount of compound 3 to that of the polar solvent for dissolving the filter cake is 1 g/3 to 8 ml, preferably 1 g/3 to 7 ml; the molar ratio of compound 3 to the resolving reagent is 1:1 to 4, preferably 1:1 to 3.

In Step 4, the ether solvent is tetrahydrofuran, 2-methyltetrahydrofuran, methyl tert-butyl ether, 1,4-dioxane or ether, preferably tetrahydrofuran, 2-methyltetrahydrofuran, methyl tert-butyl ether or 1,4-dioxane, optimally 2-methyltetrahydrofuran or 1,4-dioxane; the inorganic acid is sulphuric acid, hydrochloric acid or phosphoric acid, preferably sulfuric acid or hydrochloric acid, optimally sulfuric acid;

the ratio of the use amount of compound 4 to that of the ether solvent is 1 g/3 to 8 ml, preferably 1 g/3 to 6 ml; and the molar ratio of compound 4 to N,N-diisopropylethylamine is 1:0.8 to 2.5, preferably 1:0.8 to 2.

In Step 5, the ether solvent is tetrahydrofuran, 2-methyltetrahydrofuran, methyl tert-butyl ether, 1,4-dioxane or ether, preferably tetrahydrofuran, 2-methyltetrahydrofuran or methyl tert-butyl ether, optimally tetrahydrofuran or 2-methyltetrahydrofuran; the chloroformate is methyl chloroformate, ethyl chloroformate, or propyl chloroformate, preferably methyl chloroformate or ethyl chloroformate, optimally ethyl chloroformate; the alkaline reagent is triethylamine, sodium carbonate, potassium carbonate, sodium bicarbonate, potassium bicarbonate, sodium hydroxide or potassium hydroxide, preferably triethylamine, sodium carbonate, potassium carbonate, sodium hydroxide or potassium hydroxide, optimally triethylamine;

the ratio of the use amount of compound 5 to that of the ether solvent is 1 g/6 to 12 ml, preferably 1 g/8 to 12 ml; the molar ratio of compound 5 to N,N-diisopropylethylamine is 1:1.5 to 4, preferably 1:2 to 4; the molar ratio of compound 5 to the chloroformate is 1:1 to 2.5, preferably 1:1 to 2; and the molar ratio of compound 5 to hydrogen chloride in the hydrochloride ethanol solution is 1:1.5 to 4.5, preferably 1:2 to 4.

In Step 6, the polar solvent is acetonitrile, methanol, ethanol, acetone or tetrahydrofuran, preferably methanol, ethanol or acetone, optimally acetone; the catalyst is sodium iodide or potassium iodide, preferably potassium iodide; the trinitride is sodium azide or azidotrimethylsilane, preferably sodium azide;

the ratio of the use amount of compound 6 to that of the polar solvent is 1 g/6 to 12 ml, preferably 1 g/8 to 12 ml; the molar ratio of compound 6 to the trinitride is 1:1 to 3, preferably 1:1 to 2.5; and the molar ratio of compound 6 to the catalyst is 1:0.05 to 0.6, preferably 0.1 to 0.5.

In Step 7, the ether solvent is tetrahydrofuran, 2-methyltetrahydrofuran, methyl tert-butyl ether, 1,4-dioxane or ether, preferably tetrahydrofuran, 2-methyltetrahydrofuran, methyl tert-butyl ether, or 1,4-dioxane, optimally tetrahydrofuran; the acid reagent is citric acid, p-toluenesulfonic acid, benzenesulfonic acid, formic acid, acetic acid, hydrochloric acid, sulfuric acid or phosphoric acid, preferably citric acid, p-toluenesulfonic acid, benzenesulfonic acid, hydrochloric acid or sulfuric acid, optimally citric acid or hydrochloric acid;

the ratio of the use amount of compound 7 to that of the ether solvent is 1 g/5 to 12 ml, preferably 1 g/6 to 12 ml; the molar ratio of compound 7 to triphenylphosphine is 1:0.6 to 2, preferably 1:0.8 to 2; the ratio of the use amount of compound 7 to that of water is 1:0.6 to 2, preferably 1:0.8 to 2; the mass ratio of compound 7 to 5% palladium on carbon or 10% palladium on carbon or Raney nickel is 1:0.05 to 0.4, preferably 1:0.05 to 0.3; the hydrogen is introduced until the pressure of the system is 0.5 to 0.8 MPa, preferably 0.6 to 0.8 MPa.

In Step 8, the alcoholic solvent is methanol, ethanol, propanol or isopropanol, preferably methanol, ethanol or isopropanol, optimally isopropanol or ethanol; the catalyst is sodium iodide or potassium iodide, preferably sodium iodide; the alkaline reagent is triethylamine, diisopropylethylamine, diisopropylamine, pyridine, sodium bicarbonate, potassium bicarbonate, sodium carbonate, potassium carbonate or cesium carbonate, preferably triethylamine, pyridine, sodium bicarbonate, potassium bicarbonate, sodium carbonate or potassium carbonate, optimally triethylamine; the buffer solution is a sodium dihydrogen phosphate-disodium hydrogen phosphate aqueous solution, a potassium dihydrogen phosphate-dipotassium hydrogen phosphate aqueous solution or an ammonium formate-ammonia aqueous solution, preferably the sodium dihydrogen phosphate-disodium hydrogen phosphate aqueous solution or the potassium dihydrogen phosphate-dipotassium hydrogen phosphate aqueous solution, optimally the potassium dihydrogen phosphate-dipotassium hydrogen phosphate aqueous solution;

the ratio of the use amount of compound 8 to that of the alcoholic solvent is 1 g/6 to 12 ml, preferably 1 g/6 to 10 ml; the ratio of the use amount of compound 8 to that of pure water is 1 g/1 to 4 ml, preferably 1 g/1 to 3 ml; the molar ratio of compound 8 to compound A is 1:1 to 1.4, preferably 1:1 to 1.2; the molar ratio of compound 8 to the catalyst is 1:0.1 to 0.4, preferably 1:0.1 to 0.3; and the molar ratio of compound 8 to the alkaline reagent is 1:4 to 7, preferably 1:4 to 6.

In Step 9, the catalyst is Raney nickel, 5% palladium on carbon, 10% palladium on carbon, platinum dioxide or 20% palladium on carbon, preferably Raney nickel, 5% palladium on carbon or 10% palladium on carbon, optimally Raney nickel; the polar solvent is pure water, methanol or ethanol, preferably pure water and methanol, optimally pure water; the alkaline solution is sodium hydroxide, potassium hydroxide, sodium carbonate or potassium carbonate, preferably sodium hydroxide or sodium carbonate, optimally sodium hydroxide;

the ratio of the use amount of compound 9 to that of the polar solvent is 1 g/25 to 45 ml, preferably 1 g/30 to 40 ml and the mass ratio of compound 9 to the catalyst is 1:0.05 to 0.5, preferably 1:0.1 to 0.4;

In Step 10, the catalyst is Raney nickel, 5% palladium on carbon, 10% palladium on carbon, platinum dioxide or 20% palladium on carbon, preferably Raney nickel, platinum dioxide or 20% palladium on carbon, optimally 20% palladium on carbon; the alcoholic solvent is methanol, ethanol, isopropanol or n-butanol, preferably methanol, ethanol or isopropanol, optimally methanol; the ketone solvent is acetone or butanone, preferably acetone;

the mass ratio of compound 10 to the catalyst is 1:0.05 to 0.5, preferably 1:0.1 to 0.4; the molar ratio of compound 10 to hydrochloric acid is 1:4 to 9, preferably 1:5 to 8; and the ratio of the use amount of compound 10 to that of the alcoholic solvent or the ketone solvent is 1 g/5 to 20 ml, preferably 1 g/10 to 20 ml.

The present disclosure has the following advantages: 1. raw materials applied by the synthesis method are readily available, and the cost is significantly reduced compared with the prior art; 2. the route of the present disclosure is simple, thus greatly reducing a synthesis route of sapropterin dihydrochloride; 3. technological conditions are stable, the whole operation process is simple with less discharge of waste water, waste gas, and waste residues, and less pollution, hence providing an effective scheme for mass industrial production of sapropterin dihydrochloride; 4. the present disclosure, which resolves a racemate intermediate or an intermediate having a low antimer isomerism value by using a chiral resolving reagent to obtain an intermediate having a high antimer isomerism value, is a supplement to a chiral route; 5. the present disclosure can obtain a target product with a purity higher than 98% and an enantiomeric excess as high as more than 98%.

BRIEF DESCRIPTION OF THE DRAWINGS

The accompanying drawings of the specification are used for providing further understanding to the present disclosure and constitute a part of the present disclosure. The exemplary embodiments of the present disclosure and the illustrations thereof are used for explaining the present disclosure, instead of constituting an improper limitation to the present disclosure. In the accompanying drawings:

FIG. 1 is a flowchart of a chiral preparation process of a sapropterin dihydrochloride compound involved in the present disclosure.

DETAILED DESCRIPTION

It should be noted that, if there is no conflict, the embodiments in the present disclosure and the characteristics in the embodiments can be combined with one another. The present disclosure will be described in details below with reference to the accompanying drawings and in combination with the embodiments.

The ranges in the embodiments are caused by certain fluctuation of the temperatures and pH values as reactions progress in an experiment.

Embodiment 1 main raw material:

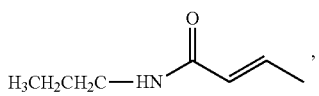

R=—CH$_2$CH$_2$CH$_3$ and X=NH

Step 1: add 950 L (10 g/ml) of pure water, and 95 kg (1eq) of crotonyl propylamine

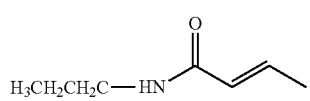

to a 2000 L reaction kettle, increase the system temperature to 40±5° C., add 208 kg (1.5eq) of N-bromobutanimide, react for 3 hours while preserving the temperature, add 300 kg (1.5eq) of a sodium hydroxide solution having a concentration of 15% to the system, react for 3.5 hours while preserving the temperature, perform extraction and concentration to obtain 67.6 kg of a compound 2,3 epoxy-butyryl propylamine, with a yield of 63%;

Step 2: in the presence of 219 kg of (8eq) acetone, add 25 kg (0.4eq) of aluminium chloride to a 2000 L reaction kettle, control the temperature at 20±5° C., add 67.6 kg (1.0eq) of 2,3 epoxy-butyryl propylamine

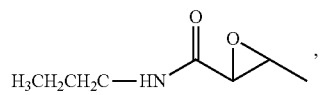

react for 8 hours while preserving the temperature, add 939 kg of a sodium carbonate (1.5eq) solution having a concentration of 8% to the system, and perform liquid separation, extraction, and concentration in the system to obtain 75.1 kg of 2,3-acetonide-propylbutyramide

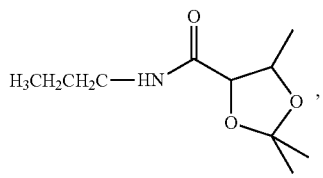

with a yield of 79%;

Step 3: add 450.6 (6 ml/g) of tetrahydrofuran, and 75.1 kg (1eq) of 2,3-acetonide-propylbutyramide

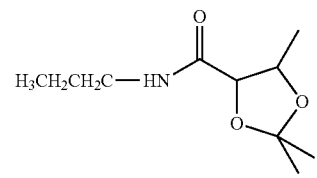

to a 1000 L reaction kettle, increase the temperature to 30±5° C., add 11.3 kg (1.2eq) of pure water and 117.2 kg (1.2eq) of a methanol solution of sodium methoxide having a concentration of 29%, react for 6 hours while preserving the temperature, perform centrifugation, dissolve a filter cake in 525.7 L (7 ml/g) of tetrahydrofuran, add 127.1 kg (2eq) of L-α-phenylethylamine, preserve the temperature at 22±5° C. for 4 hours, and perform centrifugation and drying to obtain 27.3 kg of 1-phenylethanamine 2,2,5-trimethyl-1,3-dioxolane-4-carboxylate

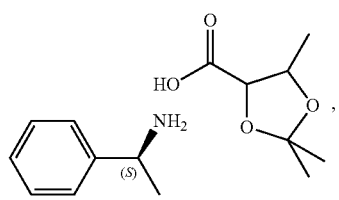

with a yield of 26%;

Step 4: add 28 L (5 ml/g) of 2-methyltetrahydrofuran, and 5.6 kg (1eq) of 1-phenylethanamine 2,2,5-trimethyl-1,3-dioxolane-4-carboxylate

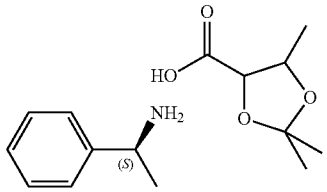

to a 72 L reaction bottle, then add a dilute hydrochloric acid aqueous solution having a concentration of 8% to the system to regulate the pH at 2±0.5, control the temperature at 0±5° C., react for 1 hour while preserving the temperature, perform liquid separation to obtain an organic phase, add 4.5 kg of (1eq) N,N-diisopropylethylamine to the organic phase, and concentrate the system to obtain 3.0 kg of (4S,5S)-2,2,5-trimethyl-1,3-dioxolan-4-methanoic acid

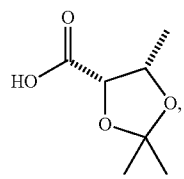

with a yield of 95%;

Step 5: add 30 L (10 ml/g) of 2-methyltetrahydrofuran, 3.0 kg of (4S,5S)-2,2,5-trimethyl-1,3-dioxolan-4-methanoic acid

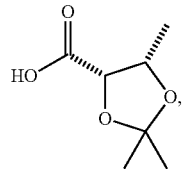

and 4.3 kg (2eq) of N,N-diisopropylethylamine to a 72 L reaction bottle, reduce the temperature to −20±5° C., add 2.7 kg (1.3eq) of ethyl chloroformate, react for 1.5 hours while preserving the temperature, introduce a diazomethane gas for 1.5 hours, add 10.3 kg (3eq) of a hydrochloride ethanol solution having a concentration of 20%, react for 1.5 hours, add triethylamine to regulate the pH value to 8±0.5, and perform extraction, liquid separation and concentration to obtain 3.1 kg of (4S,5S)-2,2,5-trimethyl-5-chloroacetyl-1,3-dioxolane

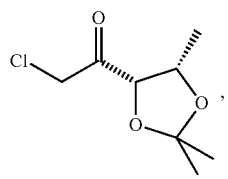

with a yield of 85%;

Step 6: add 31 L (10 ml/g) of acetone, 3.1 kg of (4S,5S)-2,2,5-trimethyl-5-chloroacetyl-1,3-dioxolane

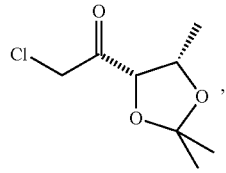

1.9 kg (1.8eq) of sodium azide, and 0.5 kg (0.2eq) of sodium iodide to a 72 L bottle, react the system for 25 hours while preserving the temperature at 30±5° C., perform filtering and concentration to obtain an acetone solution containing 3.05 kg of (4S,5S)-2,2,5-trimethyl-5-(2-azidoacetyl)-1,3-dioxolane

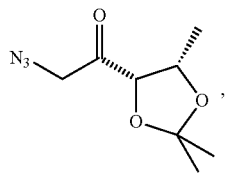

with a yield of 95%;

Step 7: add 30.5 L (10 ml/g) of tetrahydrofuran, 4.4 kg (1.1eq) of triphenylphosphine, and 0.3 kg (1.1eq) of water to a 100 L reaction kettle, regulate the pH of the system to 3±0.5 with citric acid, add the acetone solution containing 3.05 kg (1 eq) of (4S,5S)-2,2,5-trimethyl-5-(2-azidoacetyl)-1,3-dioxolane

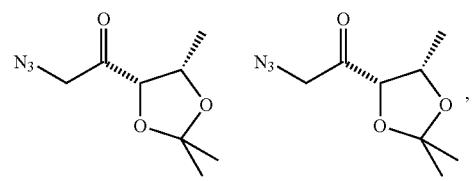

preserve the temperature at 20±5° C., react for 8 hours, perform suction filtration and concentration to obtain a filtrate containing 1.8 kg of (3S,4S)-1-amino-3,4-dihydroxy-2-pentanone

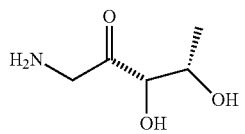

which is directly used in the next step, with a yield of 90%;

Step 8: add 18.9 L (9 ml/g) of isopropanol, 2.3 L (1.1 ml/g) of pure water, 0.1 kg of (0.1eq) of sodium iodide, 1.76 kg (1.1eq) of compound A (2-amino-6-chloro-5-nitro-3H-pyri midin-4-one), 0.92 kg (1eq) of (3S,4S)-1-amino-3,4-dihydroxy-2-pentanone

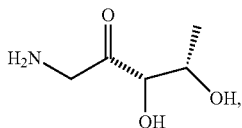

and 3.5 kg (5eq) of triethylamine to a 50 L reaction bottle, react the system for 6 hours while preserving the temperature at 50±5° C., then add a potassium dihydrogen phosphate-dipotassium hydrogen phosphate aqueous solution to regulate the pH of the system to 7±0.5; and filter the system to obtain 1.02 kg of 2-acetylamino-5-nitro-6-((3S,4S)-3,3-dihydroxy-2-oxo-pentylamino)-pyrimidin-4-one

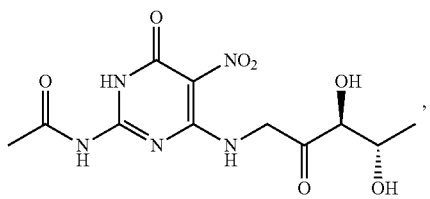 [SMILES: CC(=O)Nc1nc(NCC(=O)[C@@H](O)[C@H](C)O)c([N+](=O)[O-])c(=O)[nH]1]

with a yield of 45%;

Step 9: add 2.0 kg (1eq) of 2-acetylamino-5-nitro-6-((3S,4S)-3,3-dihydroxy-2-oxo-pentylamino)-pyrimidin-4-one

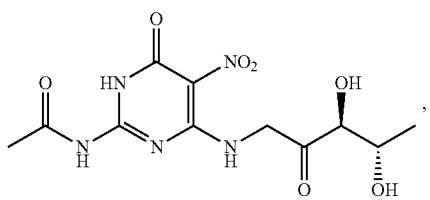 [SMILES: CC(=O)Nc1nc(NCC(=O)[C@@H](O)[C@H](C)O)c([N+](=O)[O-])c(=O)[nH]1]

70 L (35 ml/g) of pure water and 0.6 kg (0.3 g/g) of Raney nickel to a 100 L autoclave, introduce hydrogen until the pressure of the reaction system is 0.6±0.05 MPa, control the temperature of the system at 20±5° C. and the pressure at 0.6±0.05 MPa, react for 20 hours, filter the system, and regulate the pH to 11.5±0.5 to obtain of an aqueous solution containing 1.7 kg of acetylamino-7,8-dihydropteridine

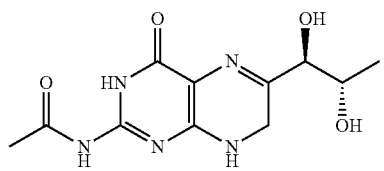 [SMILES: CC(=O)Nc1nc2c(c(=O)[nH]1)N=C([C@@H](O)[C@H](C)O)CN2]

which is used directly in the next step;

Step 10: add 0.255 kg (0.15 g/g) of 20% palladium on carbon to the aqueous solution containing 1.7 kg of acetylamino-7,8-dihydropteridine

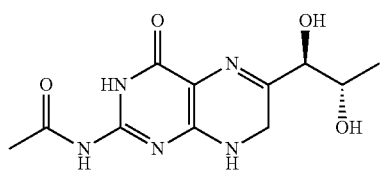 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.6±0.05 MPa, control the temperature of the system at 20±5° C. and the pressure at 0.6±0.05 MPa, react for 80 hours, after reacting thoroughly, perform quenching in 10.29 kg (7eq) of dilute hydrochloric acid having a concentration of 15%, and perform suction filtration and drying to the system to obtain a target product, i.e. a sapropterin dihydrochloride crude product of

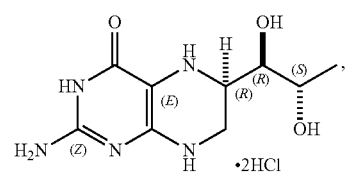

recrystallize and purify the crude product by 25 L (14.7 ml/g) of methanol at 20±5° C. to obtain 0.95 kg of a pure product, with a yield of 50%, a purity of 98.5% and an enantiomeric excess of 99.2%.

Embodiment 2 main raw material

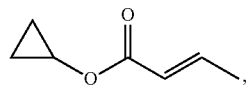

R=

and X=O

Step 1: add 2016 L (20 g/ml) of methanol, and 100.8 kg (1eq) of crotonate cyclopropylalkyl ester

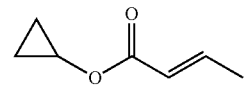

to a 3000 L reaction kettle, increase the system temperature to 50±5° C., add 414 kg (3eq) of meta-chloroperoxybenzoic acid, react for 5 hours while preserving the temperature, add 673 kg (3eq) of a potassium hydroxide solution having a concentration of 20% to the system, react for 4 hours while preserving the temperature, perform extraction and concentration to obtain 69.4 kg of a compound 2,3 epoxy-cyclopropylalkyl butyrater

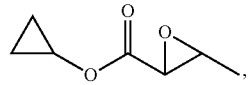

with a yield of 61%;

Step 2: in the presence of 425 kg of (15eq) acetone, add 79.2 kg (1eq) of ferric chloride to a 2000 L reaction kettle, control the temperature at 30±5° C., add 69.4 kg (1.0eq) of 2,3 epoxy-cyclopropylalkyl butyrate

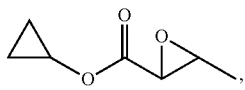

react for 10 hours while preserving the temperature, add 1552 kg of a sodium carbonate (3eq) solution having a concentration of 10% to the system, and perform liquid separation, extraction, and concentration in the system to obtain 75.3 kg of 2,3-acetonide-cyclopropylalkyl butyrate

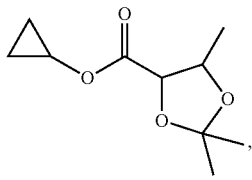

with a yield of 77%;

Step 3: add 753 (10 ml/g) of methanol, and 75.3 kg (1eq) of 2,3-acetonide-cyclopropylalkyl butyrate

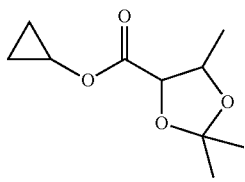

to a 1000 L reaction kettle, increase the temperature to 40±5° C., add 20.2 kg (3eq) of pure water and 210 kg (2eq) of a potassium hydroxide solution having a concentration of 20%, react for 8 hours while preserving the temperature, perform centrifugation, dissolve a filter cake in 753 L (10 ml/g) of methanol, add 322 kg (5eq) of L-α-amphetamine, preserve the temperature at 30±5° C. for 5 hours, and perform centrifugation and drying to obtain 27.2 kg of

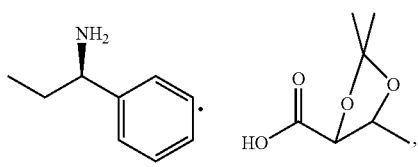

with a yield of 24.5%;

Step 4: add 27 L (10 ml/g) of tetrahydrofuran, 2.7 kg (1eq) of (4S,5S)-2,2,5-trimethyl-1,3-dioxolan-4-phenylpropylamino carboxylate

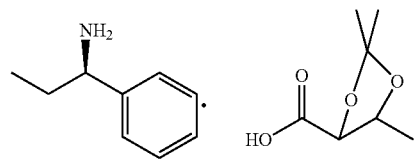

to a 72 L reaction bottle, then add a dilute hydrochloric acid aqueous solution having a concentration of 10% to the system to regulate the pH at 3±0.5, control the temperature at 10±5° C., react for 1 hour, perform liquid separation to obtain an organic phase, add 6.1 kg of (3eq) N,N-diisopropylethylamine to the organic phase, and concentrate the system to obtain 1.3 kg of (4S,5S)-2,2,5-trimethyl-1,3-dioxolan-4-methanoic acid

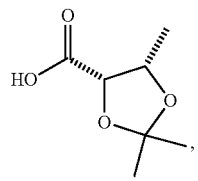

with a yield of 90%;

Step 5: add 20 L (15 ml/g) of tetrahydrofuran, 1.3 kg of (4S,5S)-2,2,5-trimethyl-1,3-dioxolan-4-methanoic acid

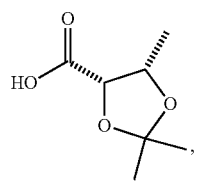

and 8 kg (5eq) of N,N-diisopropylethylamine to a 72 L reaction bottle, reduce the temperature to 0±5° C., add 2.9 kg (3eq) of propyl chloroformate, react for 1 to 2 hours while preserving the temperature, introduce a diazomethane gas for 2 hours, add 12.7 kg (5eq) of a hydrochloride ethanol solution having a concentration of 20%, react for 2 hours, add sodium carbonate to regulate the pH value to 9±0.5, and perform extraction, liquid separation and concentration to obtain 1.3 kg of (4S,5S)-2,2,5-trimethyl-5-chloroacetyl-1,3-dioxolane

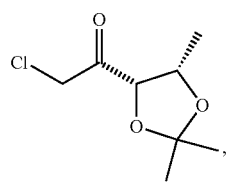

with a yield of 82%;

Step 6: add 19.5 L (15 ml/g) of acetonitrile, 1.3 kg of (4S,5S)-2,2,5-trimethyl-5-chloroacetyl-1,3-dioxolane

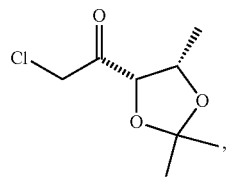

3.1 kg (4eq) of azidotrimethylsilane, and 0.8 kg (0.8eq) of sodium iodide to a 72 L bottle, react the system for 30 hours while preserving the temperature at 40±5° C., perform filter ing and concentration to obtain an acetonitrile solution containing 1.21 kg of

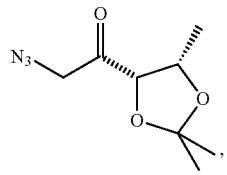

with a yield of 90%;

Step 7: add 18.2 L (15 ml/g) of 1,4-dioxane and 0.73 kg (0.6 g/g) of Raney nickel to a 50 L reaction kettle, introduce hydrogen until the system pressure is 0.9±0.1 MPa, regulate the pH of the system to 1±0.5 with concentrated hydrochloric acid, add the acetonitrile solution containing 1.21 kg (1eq) of (4S,5S)-2,2,5-trimethyl-5-(2-azidoacetyl)-1,3-dioxolane

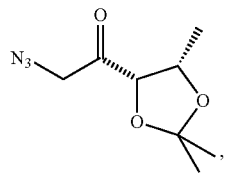

react at 30±5° C. for 8 hours, perform suction filtration and concentration to obtain 0.71 kg of (3S,4S)-1-amino-3,4-dihydroxy-2-pentanone

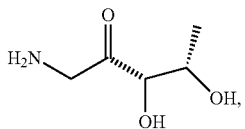

with a yield of 87.5%;

Step 8: add 47.5 L (15 ml/g) of methanol, 15.8 L (5 ml/g) of pure water, 1.28 kg of (0.5eq) of potassium iodide, 3.6 kg (1.5eq) of compound A (2-amino-6-chloro-5-nitro-3H-pyrimidin-4-one), 1.4 kg (1eq) of (3S,4S)-1-amino-3,4-dihydroxy-2-pentanone

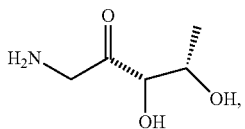

and 6.4 kg (8eq) of pyridine to a 100 L reaction bottle, react the system for 8 hours while preserving the temperature at 80±5° C., then add an ammonium formate-ammonia aqueous solution to regulate the pH of the system to 8±0.5; and filter the system to obtain 1.47 kg of 2-acetylamino-5-nitro-6-((3S,4S)-3,3-dihydroxy-2-oxo-pentylamino)-pyrimidin-4-one

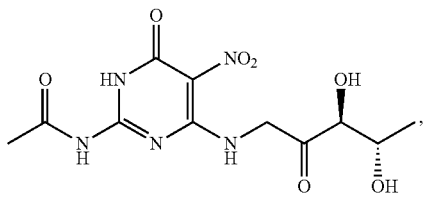 [SMILES: CC(=O)Nc1nc(NCC(=O)[C@@H](O)[C@H](C)O)c([N+](=O)[O-])c(=O)[nH]1]

with a yield of 43.2%;

Step 9: add 2.94 kg (1eq) of 2-acetylamino-5-nitro-6-((3S,4S)-3,3-dihydroxy-2-oxo-pentylamino)-pyrimidin-4-one

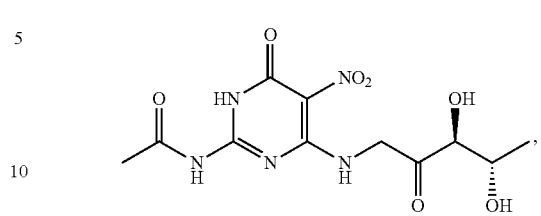

147 L (50 ml/g) of methanol and 1.76 kg (0.6 g/g) of 5% palladium on carbon to a 200 L autoclave, introduce hydrogen until the pressure of the system is 0.9±0.05 MPa, control the temperature of the system at 30±5° C. and the pressure at 0.9±0.05 MPa, react for 24 hours, filter the system, and regulate the pH to 12±0.5 to obtain a methanol solution containing 2.5 kg of acetylamino-7,8-dihydropteridine

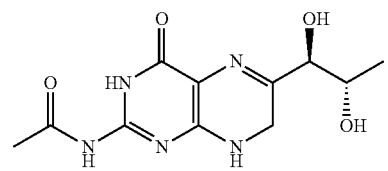 [SMILES: CC(=O)Nc1nc2c(c(=O)[nH]1)N=C([C@@H](O)[C@H](C)O)CN2]

which is used directly in the next step;

Step 10: add 1.5 kg (0.6 g/g) of Raney nickel to the methanol solution containing 2.5 kg of acetylamino-7,8-dihydropteridine

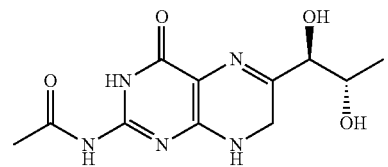 [SMILES: CC(=O)Nc1nc2c(c(=O)[nH]1)N=C([C@@H](O)[C@H](C)O)CN2]

obtained in Step 9, introduce hydrogen until the pressure of the system is 0.9±0.05 MPa, control the temperature of the system at 30±5° C. and the pressure at 0.9±0.05 MPa, react for 84 hours, after reacting thoroughly, perform quenching in 16.2 kg (10eq) of dilute hydrochloric acid having a concentration of 20%, and perform suction filtration and drying to the system to obtain a target product, i.e. a crude product of sapropterin dihydrochloride

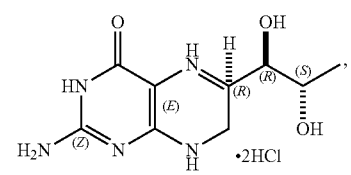

recrystallize and purify the crude product by 62.5 L (25 ml/g) of acetone at 40±5° C. to obtain 1.31 kg of a pure product, with a yield of 47%, a purity of 98.1% and an enantiomeric excess of 98.9%.

Embodiment 3 main raw material:

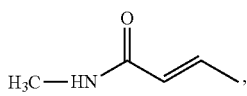

R=—CH₃ and X=NH

Step 1: add 495 L (5 g/ml) of ethanol, and 99 kg (1eq) of crotonyl methanamine

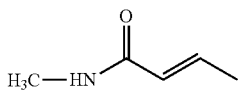

to a 2000 L reaction kettle, increase the system temperature to 35±5° C., add 180.2 kg (1eq) of a tert-butyl hydroperoxide toluene solution having a concentration of 50%, react for 2 hours while preserving the temperature, add 400 kg (1eq) of a sodium hydroxide solution having a concentration of 10% to the system, react for 3 hours while preserving the temperature, perform extraction and concentration to obtain 70.2 kg of 2,3 epoxy-butyryl methylamine

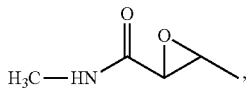

with a yield of 61%;

Step 2: in the presence of 106 kg of (3eq) acetone, add 2.6 kg (0.1eq) of lithium chloride to a 1000 L reaction kettle, control the temperature at 10±5° C., add 70.2 kg (1.0eq) of 2,3 epoxy-butyryl methylamine, react for 5 hours while preserving the temperature, add 610 kg of a potassium bicarbonate (0.5eq) solution having a concentration of 5% to the system, and perform liquid separation, extraction, and concentration in the system to obtain 81.3 kg of 2,3-acetonide-alkylformamide

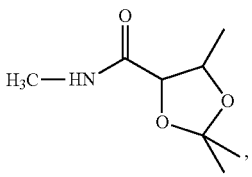

with a yield of 77%;

Step 3: add 243.9 L-(3 ml/g) of ethanol, and 81.3 kg (1eq) of 2,3-acetonide-alkylformamide

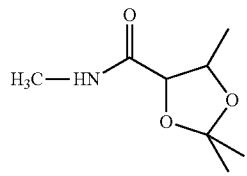

to a 1000 L reaction kettle, increase the temperature to 250±5° C., add 4.23 kg (0.5eq) of pure water and 47 kg (0.5eq) of a sodium hydroxide solution having a concentration of 20%, react for 3 hours while preserving the temperature, perform centrifugation, dissolve a filter cake in 122.6 L (2 ml/g) of ethanol, add 56.9 kg (1eq) of L-α-phenylethylamine, preserve the temperature at 15±5° C. for 3 hours, and perform centrifugation and drying to obtain 32.3 kg of (4S,5S)-2,2,5-trimethyl-1,3-dioxolan-4-phenylpropylamino carboxylate

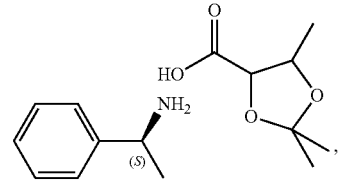

with a yield of 24.5%;

Step 4: add 30 L (3 ml/g) of 1,4-dioxane, 10 kg (1eq) of (4S,5S)-2,2,5-trimethyl-1,3-dioxolan-4-phenylpropylamino carboxylate

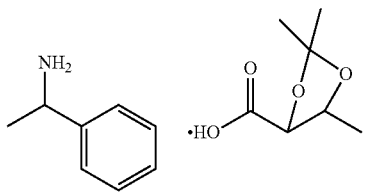

to a 72 L reaction bottle, then add a dilute phosphoric acid aqueous solution having a concentration of 5% to the system to regulate the pH at 1±0.5, control the temperature at −10±5° C., react for 1 hour, perform liquid separation to obtain an organic phase, add 3.3 kg of (0.8eq) N,N-diisopropylethylamine to the organic phase, and concentrate the system to obtain 5.2 kg of (4S,5S)-2,2,5-trimethyl-1,3-dioxolan-4-methanoic acid

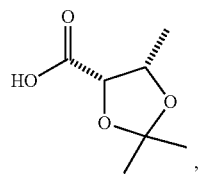

with a yield of 91%;

Step 5: add 26 L (5 ml/g) of 1,4-dioxane, 5.2 kg (1eq) of (4S,5S)-2,2,5-trimethyl-1,3-dioxolan-4-methanoic acid

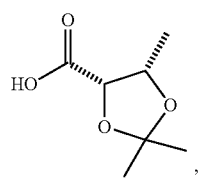

and 3.7 kg (1eq) of N,N-diisopropylethylamine to a 72 L reaction bottle, reduce the temperature to −30±5° C., add 3.1 kg (1eq) of methyl chloroformate, react for 1 hour while preserving the temperature, introduce a diazomethane gas for 1 hour, add 2 kg (1 eq) of a hydrochloride ethanol solution having a concentration of 20%, react for 1 hour, add potassium bicarbonate to regulate the pH value to 7±0.5, and perform extraction, liquid separation and concentration to obtain 5 kg of (4S,5S)-2,2,5-trimethyl-5-chloroacetyl-1,3-dioxolane

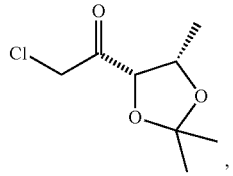

with a yield of 81%;

Step 6: add 25 L (5 ml/g) of methanol, 5 kg of (4S,5S)-2,2,5-trimethyl-5-chloroacetyl-1,3-dioxolane

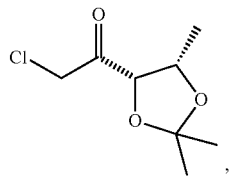

1.7 kg (1eq) of sodium azide, and 0.22 kg (0.05eq) of potassium iodide to a 72 L bottle, after react the system for 20 hours while preserving the temperature at 15±5° C., perform filtering and concentration to obtain a methanol solution containing 4.5 kg of (4S,5S)-2,2,5-trimethyl-5-(2-azidoacetyl)-1,3-dioxolane

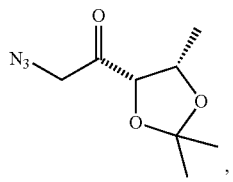

with a yield of 87%;

Step 7: add 22.5 L (5 ml/g) of methyl tert-butyl ether and 0.3 kg (0.05 g/g) of 10% palladium on carbon to a 100 L reaction kettle, introduce hydrogen until the system pressure is 0.4±0.1 MPa, regulate the pH of the system to 4±0.5 with benzenesulfonic acid, add the methanol solution containing 4.5 kg (1 eq) of (4S,5S)-2,2,5-trimethyl-5-(2-azidoacetyl)-1,3-dioxolane

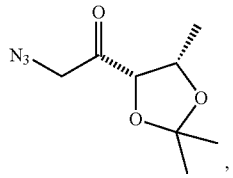

preserve the temperature at 10±5° C., react for 5 hours, perform suction filtration and concentration to obtain a filtrate containing 2.6 kg of (3S,4S)-1-amino-3,4-dihydroxy-2-pentanone

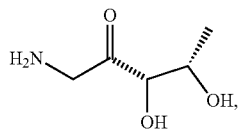

with a yield of 86%;

Step 8: add 21 L (5 ml/g) of ethanol, 4.2 L (1 ml/g) of pure water, 0.1 kg of (0.05eq) sodium iodide, 3.2 kg (1eq) of compound A (2-amino-6-chloro-5-nitro-3H-pyrimidin-4-one), 1.83 kg (1eq) of (3S,4S)-1-amino-3,4-dihydroxy-2-pentanone

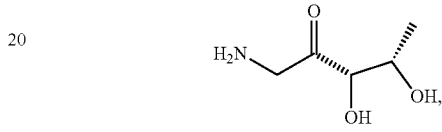

and 4.4 kg (3eq) of sodium carbonate to a 50 L reaction bottle, react the system for 4 hours while preserving the temperature at 30±5° C., then add a sodium dihydrogen phosphate-disodium hydrogen phosphate aqueous solution to regulate the pH of the system to 6±0.5; and filter the system to obtain 1.9 kg of 2-acetylamino-5-nitro-6-((3S,4S)-3,3-dihydroxy-2-oxo-pentylamino)-pyrimidin-4-one

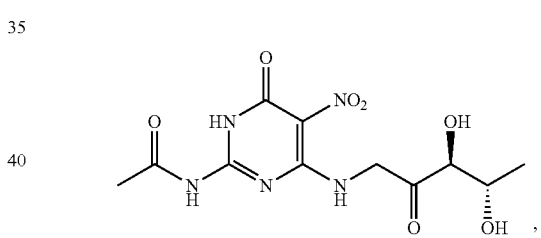

with a yield of 42%;

Step 9: add 3.8 kg (1eq) of 2-acetylamino-5-nitro-6-((3S,4S)-3,3-dihydroxy-2-oxo-pentylamino)-pyrimidin-4-one

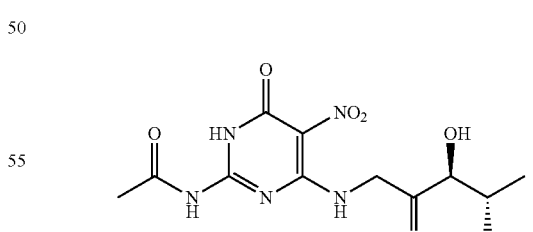

76 L (20 ml/g) of ethanol and 0.2 kg (0.05 g/g) of 20% palladium on carbon to a 100 L autoclave, introduce hydrogen until the system pressure is 0.4±0.05 MPa, control the temperature of the system at 15±5° C. and the pressure at 0.4±0.05 MPa, react for 18 hours, filter the system, and regulate the pH to 11±0.5 to obtain of an ethanol solution containing 3.25 kg of acetylamino-7,8-dihydropteridine

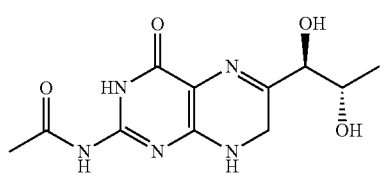 [SMILES: CC(=O)Nc1nc2c(c(=O)[nH]1)N=C([C@@H](O)[C@H](C)O)CN2]

which is used directly in the next step;

Step 10: add 0.16 kg (0.05 g/g) of platinum dioxide in the presence of the ethanol solution containing 3.25 kg of acetylamino-7,8-dihydropteridine

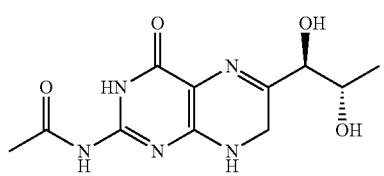 [SMILES: CC(=O)Nc1nc2c(c(=O)[nH]1)N=C([C@@H](O)[C@H](C)O)CN2]

obtained in Step 9, introduce hydrogen until the system pressure is 0.4±0.05 MPa, control the temperature of the system at 10±5° C. and the pressure at 0.4±0.05 MPa, react for 72 hours, after reacting thoroughly, perform quenching in 12.6 kg (3eq) of dilute hydrochloric acid having a concentration of 10%, and perform suction filtration and drying to the system to obtain a target product, i.e. a crude product of sapropterin dihydrochloride

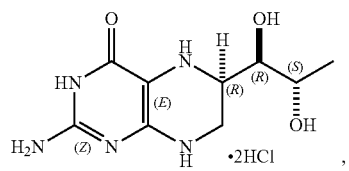

recrystallize and purify the crude product by 16.3 L (5 ml/g) of isopropanol at 0±5° C. to obtain 1.52 kg of a pure product, with a yield of 42%, a purity of 98.0% and an enantiomeric excess of 98.7%.

Embodiment 4 main raw material:

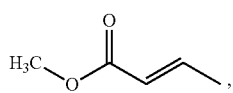

R=—CH$_3$ and X=O

Step 1: add 900 L (15 g/ml) of isopropanol, and 60 kg (1eq) of methyl crotonate

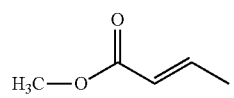

to a 2000 L reaction kettle, increase the system temperature to 45±5° C., add 178 kg (2.5eq) of N-bromobutanimide, react for 3.5 hours while preserving the temperature, add 420 kg (2.5eq) of a potassium hydroxide solution having a concentration of 20% to the system, react for 3.5 hours while preserving the temperature, perform extraction and concentration to obtain 42.6 kg of 2,3 epoxy-methyl butyrate

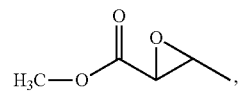

with a yield of 61.2%;

Step 2: in the presence of 256 kg of (12eq) acetone, add 40 kg (0.8eq) of zinc chloride to a 2000 L reaction kettle, control the temperature at 25±5° C., add 42.6 kg (1.0eq) of 2,3 epoxy-methyl butyrate

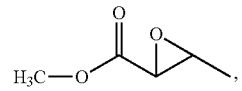

react for 9 hours while preserving the temperature, add 1408 kg of a potassium carbonate (2.5eq) solution having a concentration of 9% to the system, and perform liquid separation, extraction, and concentration in the system to obtain 49.8 kg of 2,3-acetonide-methyl butyrate

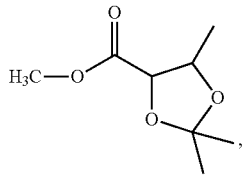

with a yield of 78%;

Step 3: add 398 (8 ml/g) of methanol, and 49.8 kg (1eq) of 2,3-acetonide-methyl butyrate

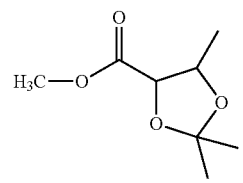

to a 1000 L reaction kettle, increase the temperature to 35±5° C., add 9.3 kg (1.8eq) of pure water and 144.5 kg (1.8eq) of a potassium hydroxide aqueous solution having a concentration of 20%, react for 6.5 hours while preserving the temperature, perform centrifugation, dissolve a filter cake in 398 L (8 ml/g) of methanol, add 154.7 kg (4eq) of L-α-amphetamine, preserve the temperature at 25±5° C. for 4.5 hours, and perform centrifugation and drying to obtain 21.1 kg of 1-phenyl-propan-1-amine (4S,5S)-2,2,5-trimethyl-1,3-dioxolane-4-carboxylate

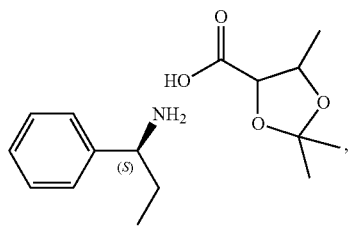

with a yield of 25%;

Step 4: add 48 L (8 ml/g) of methyl tert-butyl ether, 6 kg (1eq) of 1-phenylpropan-1-amine (4S,5S)-2,2,5-trimethyl-1,3-dioxolane-4-carboxylate

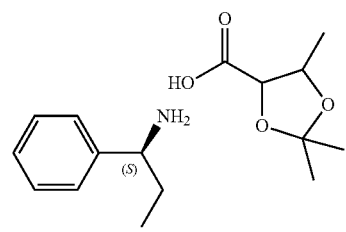

to a 72 L reaction bottle, then add a dilute hydrochloric acid aqueous solution having a concentration of 9% to the system to regulate the pH at 2.5±0.5, control the temperature at −5±5° C., react for 1 hour, perform liquid separation to obtain an organic phase, add 6.6 kg of (2.5eq) N,N-diisopropylethylamine to the organic phase, and concentrate the system to obtain 3.0 kg of 1,3-dioxolan-4-carboxylic acid

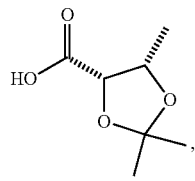

with a yield of 92%;

Step 5: add 36 L (12 ml/g) of tetrahydrofuran, 3.0 kg of (4S,5S)-2,2,5-trimethyl-1,3-dioxolan-4-methanoic acid

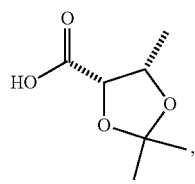

and 9.7 kg (4eq) of N,N-diisopropylethylamine to a 72 L reaction bottle, reduce the temperature to −25±5° C., add 4.4 kg (2.5eq) of methyl chloroformate, react for 1.5 hours while preserving the temperature, introduce a diazomethane gas for 1.5 hours, add 15.3 kg (4.5eq) of a hydrochloride ethanol solution having a concentration of 20%, react for 1.5 hours, add triethylamine to regulate the pH value to 8.5±0.5, and perform extraction, liquid separation and concentration to obtain 3.0 kg of (4S,5S)-2,2,5-trimethyl-5-chloroacetyl-1,3-dioxolane

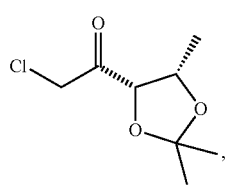

with a yield of 83%;

Step 6: add 36 L (12 ml/g) of acetone, 3 kg of (4S,5S)-2,2,5-trimethyl-5-chloroacetyl-1,3-dioxolane

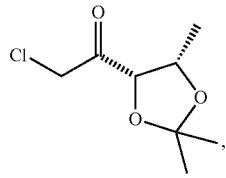

3 kg (3eq) of sodium azide, and 1.5 kg (0.6eq) of sodium iodide to a 72 L bottle, react the system for 27 hours while preserving the temperature at 32±5° C., perform filtering and concentration to obtain an acetone solution containing 2.8 kg of (4S,5S)-2,2,5-trimethyl-5-(2-azidoacetyl)-1,3-dioxolane

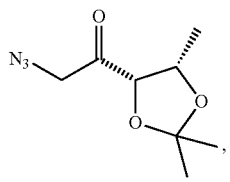

with a yield of 91%;

Step 7: add 33.7 L (12 ml/g) of 2-methyltetrahydrofuran, 8.6 kg (2.0eq) of triphenylphosphine, and 0.5 kg (2.0eq) of water to a 72 L reaction kettle, regulate the pH of the system to 3±0.5 with acetic acid, add the acetone solution containing 2.8 kg of (4S,5S)-2,2,5-trimethyl-5-(2-azidoacetyl)-1,3-dioxolane

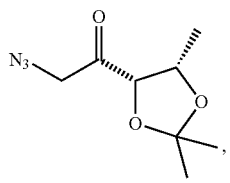

preserve the temperature at 25±5° C., react for 8.5 hours, perform suction filtration and concentration to obtain a filtrate containing 1.6 kg of (3S,4S)-1-amino-3,4-dihydroxy-2-pentanone

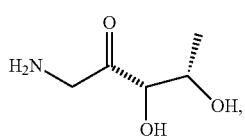

with a yield of 87.5%;

Step 8: add 19.7 L (12 ml/g) of methanol, 6.4 L (4 ml/g) of pure water, 0.8 kg of (0.4eq) of sodium iodide, 4.0 kg (1.4eq) of compound A (2-amino-6-chloro-5-nitro-3H-pyrimidin-4-one), 1.6 kg (1eq) of (3S,4S)-1-amino-3,4-dihydroxy-2-pentanone

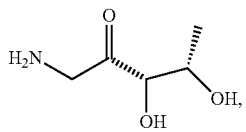

and 8.7 kg (7eq) of potassium bicarbonate to a 50 L reaction bottle, react the system for 7 hours while preserving the temperature at 70±5° C., then add a sodium dihydrogen phosphate-disodium hydrogen phosphate aqueous solution to regulate the pH of the system to 7.5±0.5; and filter the system to obtain 1.7 kg of 2-acetylamino-5-nitro-6-((3S,4S)-3,3-dihydroxy-2-oxo-pentylamino)-pyrimidin-4-one

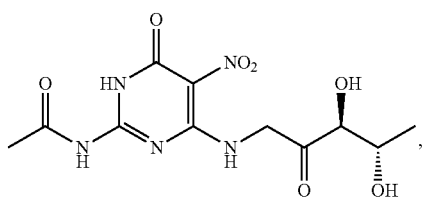 [SMILES: CC(=O)Nc1nc(NCC(=O)[C@@H](O)[C@H](C)O)c([N+](=O)[O-])c(=O)[nH]1]

with a yield of 43%;

Step 9: add 1.7 kg (1eq) of 2-acetylamino-5-nitro-6-((3S, 4S)-3,3-dihydroxy-2-oxo-pentylamino)-pyrimidin-4-one

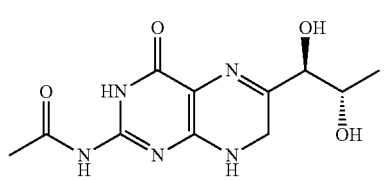 [SMILES: CC(=O)Nc1nc2c(c(=O)[nH]1)N=C([C@@H](O)[C@H](C)O)CN2]

78.7 L (45 ml/g) of methanol and 0.9 kg (0.5 g/g) of 5% palladium on carbon to a 100 L autoclave, introduce hydrogen until the reaction system pressure is 0.8±0.05 MPa, control the temperature of the system at 25±5° C. and the pressure at 0.8±0.05 MPa, react for 22 hours, filter the system, and regulate the pH to 11±0.5 to obtain a methanol solution containing 1.5 kg of acetylamino-7,8-dihydropteridine

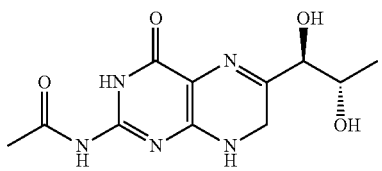 [SMILES: CC(=O)Nc1nc2c(c(=O)[nH]1)N=C([C@@H](O)[C@H](C)O)CN2]

which is used directly in the next step;

Step 10: add 0.7 kg (0.05 g/g) of 5% palladium on carbon in the presence of the methanol solution containing 1.5 kg of acetylamino-7,8-dihydropteridine

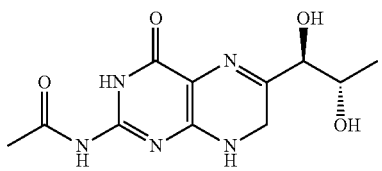 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.8±0.05 MPa, control the temperature of the system at 25±5° C. and the pressure at 0.8±0.05 MPa, react for 82 hours, after reacting thoroughly, perform quenching in 31.9 kg (9eq) of dilute hydrochloric acid having a concentration of 15%, and perform suction filtration and drying to the system to obtain a target product, i.e. a crude product of sapropterin dihydrochloride

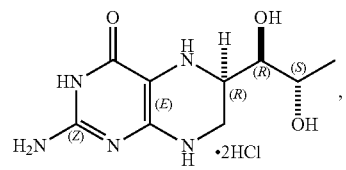

recrystallize and purify the crude product by 29 L (20 ml/g) of methanol at 35±5° C. to obtain 0.8 kg of a pure product, with a yield of 45%, a purity of 98.3% and an enantiomeric excess of 99.1%.

Embodiment 5 main raw material:

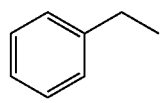

and X═O

Step 1: add 780 L (12 g/ml) of ethanol, and 65 kg (1eq) of benzyl crotonate

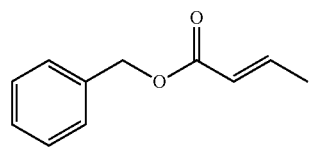

to a 2000 L reaction kettle, increase the system temperature to 42±5° C., add 127.3 kg (2eq) of meta-chloroperoxybenzoic acid, react for 3 hours while preserving the temperature, add 147.6 kg (2eq) of a sodium hydroxide solution having a concentration of 20% to the system, react for 3.2 hours while preserving the temperature, perform extraction and concentration to obtain 44 kg of 2,3-epoxy-benzyl butyrate

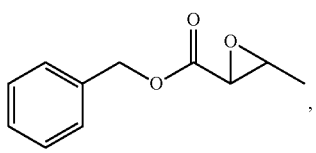

with a yield of 62%;

Step 2: in the presence of 132.8 kg of (10eq) acetone, add 5.8 kg (0.6eq) of lithium chloride to a 1000 L reaction kettle, control the temperature at 22±5° C., add 44 kg (1.0eq) of 2,3-epoxy-benzyl butyrate

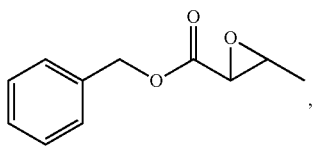

react for 7 hours while preserving the temperature, add 343 kg of a potassium dicarbonate (1.5eq) solution having a concentration of 10% to the system, and perform liquid separation, extraction, and concentration in the system to obtain 44 kg of 2,3-acetonide-benzyl butyrate

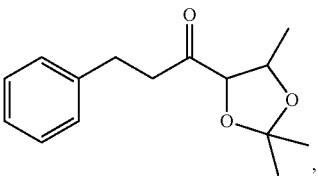 [SMILES: CC1OC(C)(C)OC1C(=O)CCc1ccccc1]

with a yield of 77.5%;

Step 3: add 352 (8 ml/g) of ethanol, and 44 kg (1 eq) of 2,3-acetonide-benzyl butyrate

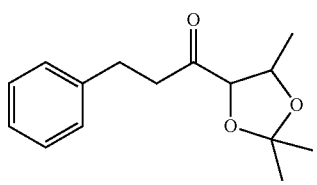 [SMILES: CC1OC(C)(C)OC1C(=O)CCc1ccccc1]

to a 1000 L reaction kettle, increase the temperature to 37±5° C., add 4.8 kg (1.5eq) of pure water and 53.2 kg (1.5eq) of a sodium hydroxide aqueous solution having a concentration of 20%, react for 6 hours while preserving the temperature, perform centrifugation, dissolve a filter cake in 352 L (8 ml/g) of ethanol, add 71.9 kg (3eq) of L-α-amphetamine, preserve the temperature at 22±5° C. for 4 hours, and perform centrifugation and drying to obtain 13.2 kg of 1-phenylpropan-1-amine (4S,5S)-2,2,5-trimethyl-1,3-dioxolane-4-carboxylate

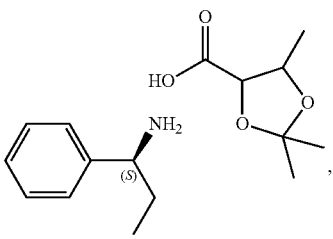

with a yield of 25.3%;

Step 4: add 48 L (6 ml/g) of 1,4-dioxane, 8 kg (1 eq) of 1-phenylpropan-1-amine (4S,5S)-2,2,5-tri methyl-1,3-dioxolane-4-carboxylate

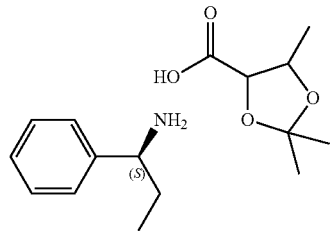

to a 72 L reaction bottle, then add a dilute sulphuric acid aqueous solution having a concentration of 10% to the system to regulate the pH at 2.5±0.5, control the temperature at −5±5° C., react for 1 hour, perform liquid separation to obtain an organic phase, add 7.0 kg of (2.0eq) N,N-diisopropylethylamine to the organic phase, and concentrate the system to obtain 4.1 kg of (4S,5S)-2,2,5-trimethyl-1,3-dioxolan-4-methanoic acid

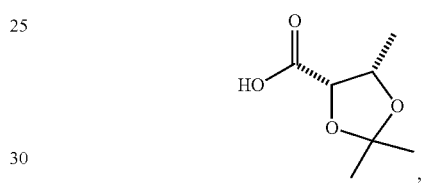

with a yield of 93.5%;

Step 5: add 49 L (12 ml/g) of 2-methyltetrahydrofuran, 4.1 kg of 1,3-dioxolan-4-carboxylic acid

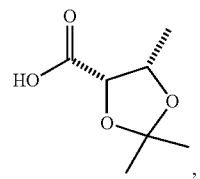

and 13.1 kg (4eq) of N,N-diisopropylethylamine to a 100 L reaction bottle, reduce the temperature to −22±5° C., add 5.5 kg (2.0eq) of ethyl chloroformate, react for 1.8 hours while preserving the temperature, introduce a diazomethane gas for 1.8 hours, add 18.5 kg (4.5eq) of a hydrochloride ethanol solution having a concentration of 20%, react for 1.8 hours, add potassium bicarbonate to regulate the pH value to 8.5±0.5, and perform extraction, liquid separation and concentration to obtain 4.1 kg of (4S,5S)-2,2,5-trimethyl-5-chloroacetyl-1,3-dioxolane

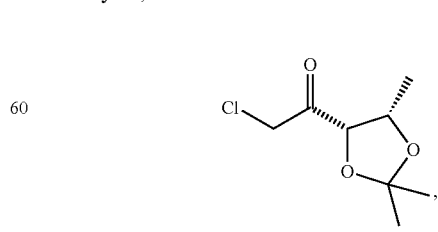

with a yield of 83.7%;

Step 6: add 49 L (12 ml/g) of acetone, 4.1 kg of (4S,5S)-2,2,5-trimethyl-5-chloroacetyl-1,3-dioxolane

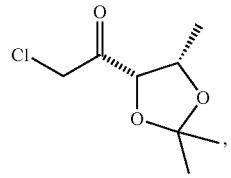

3.4 kg (2.5eq) of sodium azide, and 1.8 kg (0.5eq) of potassium iodide to a 72 L bottle, react the system for 26 hours while preserving the temperature at 34±5° C., perform filtering and concentration to obtain an acetone solution containing 3.9 kg of (4S,5S)-2,2,5-trimethyl-5-(2-azidoacetyl)-1,3-dioxolane

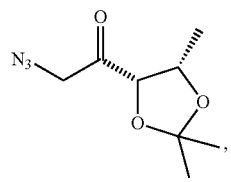

with a yield of 91.5%;

Step 7: add 46.4 L (12 ml/g) of methyl tert-butyl ether and 1.2 kg (0.3 g/g) of Raney nickel to a 100 L reaction kettle, introduce hydrogen until the system pressure is 0.8±0.1 MPa, regulate the pH of the system to 3±0.5 with concentrated sulfuric acid, add an acetonitrile solution containing 3.9 kg (1eq) of (4S,5S)-2,2,5-trimethyl-5-(2-azidoacetyl)-1,3-dioxolane

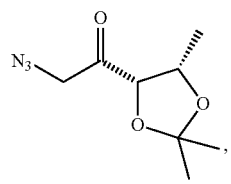

react at 27±5° C. for 8.5 hours, perform suction filtration and concentration to obtain 2.3 kg of (3S,4S)-1-amino-3,4-dihydroxy-2-pentanone

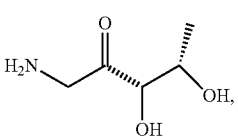

with a yield of 89%;

Step 8: add 23 L (10 ml/g) of propanol, 6.9 L (3 ml/g) of pure water, 0.9 kg of (0.3eq) of potassium iodide, 4.8 kg (1.2eq) of compound A (2-amino-6-chloro-5-nitro-3H-pyrimidin-4-one), 2.3 kg (1eq) of (3S,4S)-1-amino-3,4-dihydroxy-2-pentanone

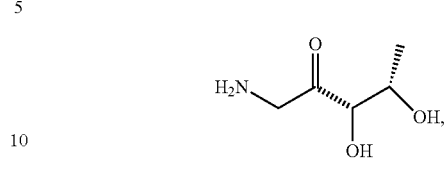

and 10.5 kg (6eq) of diisopropylamine to a 50 L reaction bottle, react the system for 7 hours while preserving the temperature at 72±5° C., then add a potassium dihydrogen phosphate-dipotassium phosphate aqueous solution to regulate the pH of the system to 7.5±0.5; and filter the system to obtain 2.5 kg of 2-acetylamino-5-nitro-6-((3S,4S)-3,3-dihydroxy-2-oxo-pentylamino)-pyrimidin-4-one

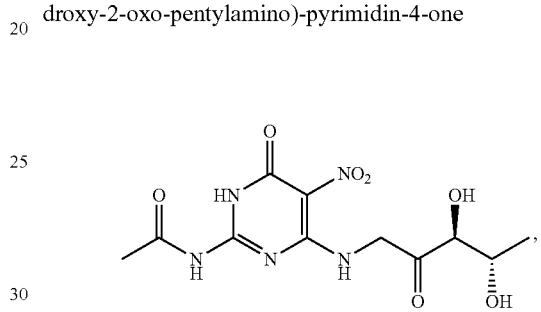

with a yield of 44%;

Step 9: add 1.25 kg (1eq) of 2-acetylamino-5-nitro-6-((3S,4S)-3,3-dihydroxy-2-oxo-pentylamino)-pyrimidin-4-one

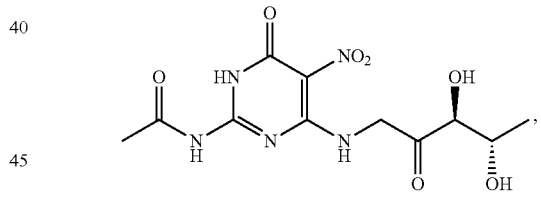

50 L (40 ml/g) of ethanol and 0.5 kg (0.4 g/g) of 10% palladium on carbon to a 100 L autoclave, introduce hydrogen until the reaction system pressure is 0.8±0.05 MPa, control the temperature of the system at 27±5° C. and the pressure at 0.8±0.05 MPa, react for 24 hours, filter the system, and regulate the pH to 11±0.5 to obtain an ethanol solution containing 1.1 kg of acetylamino-7,8-dihydropteridine

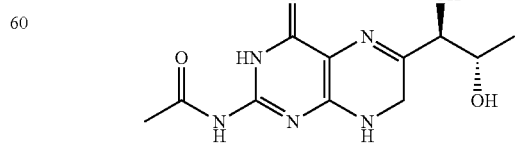

which is used directly in the next step;

Step 10: add 0.44 kg (0.4 g/g) of 10% palladium on carbon in the presence of the ethanol solution containing 1.1 kg of acetylamino-7,8-dihydropteridine

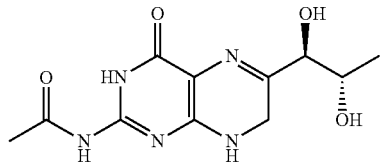 [SMILES: CC(=O)Nc1nc2c(c(=O)[nH]1)N=C([C@@H](O)[C@H](C)O)CN2]

obtained in Step 9, introduce hydrogen until the pressure of the reaction kettle is 0.8±0.05 MPa, control the temperature of the system at 25±5° C. and the pressure at 0.8±0.05 MPa, react for 80 hours, after reacting thoroughly, perform quenching in 20 kg (8eq) of dilute hydrochloric acid having a concentration of 15%, and perform suction filtration and drying to the system to obtain a target product, i.e. a crude product of sapropterin dihydrochloride

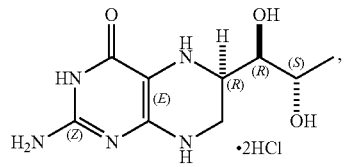

recrystallize and purify the crude product by 21.4 L (20 ml/g) of ethanol at 35±5° C. to obtain 0.4 kg of a pure product, with a yield of 46.2%, a purity of 98.5% and an enantiomeric excess of 99.2%.

Embodiment 6 main raw material:

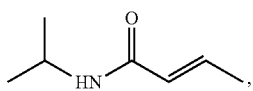

R=

and X=N

Step 1: add 510 L (6 g/ml) of methanol, and 85 kg (1eq) of (E)-N-isopropylbut-2-enamide

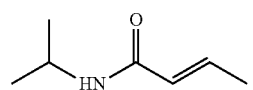

to a 2000 L reaction kettle, increase the system temperature to 37±5° C., add 120.5 kg (1eq) of tert-butyl hydroperoxide toluene solution having a concentration of 50%, react for 2.5 hours while preserving the temperature, add 133.7 kg (1eq) of a sodium hydroxide solution having a concentration of 20% to the system, react for 3.5 hours while preserving the temperature, perform extraction and concentration to obtain 59 kg of N-isopropyl-3-methyloxirane-2-carboxamide

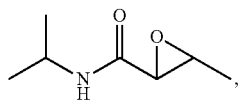

with a yield of 61.7%;

Step 2: in the presence of 119.8 kg of (5eq) acetone, add 9.3 kg (0.1eq) of zinc bromide to a 1000 L reaction kettle, control the temperature at 15±5° C., add 59 kg (1.0eq) of N-isopropyl-3-methyloxirane-2-carboxamide

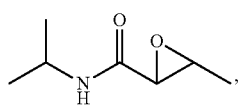

react for 6 hours while preserving the temperature, add 173 kg of a sodium dicarbonate (0.5eq) solution having a concentration of 10% to the system, and perform liquid separation, extraction, and concentration in the system to obtain 64.7 kg of N-isopropyl-2,2,5-trimethyl-1,3-dioxolane-4-carboxamide

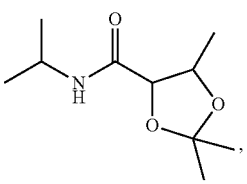

with a yield of 78%;

Step 3: add 259 (4 ml/g) of tetrahydrofuran, and 64.7 kg (1eq) of N-isopropyl-2,2,5-trimethyl-1,3-dioxolane-4-carboxamide

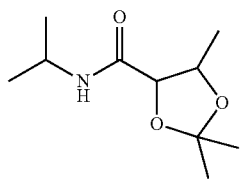

to a 1000 L reaction kettle, increase the temperature to 27±5° C., add 2.9 kg (0.5eq) of pure water and 29.9 kg (0.5eq) of a methanol solution of sodium methoxide having a concentration of 29%, react for 4 hours while preserving the temperature, perform centrifugation, dissolve a filter cake in 194 L (3 ml/g) of tetrahydrofuran, add 39 kg (1 eq) of L-α-phenylethylamine, preserve the temperature at 18±5° C. for 3.5 hours, and perform centrifugation and drying to obtain 22.4 kg of 1-phenylethanamine 2,2,5-trimethyl-1,3-dioxolane-4-carboxylate

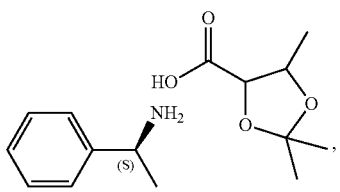

with a yield of 24.7%;

Step 4: add 30 L (3 ml/g) of 2-methyltetrahydrofuran, 10 kg (1eq) of 1-phenylethanamine-2,2,5-trimethyl-1,3-dioxolane-4-carboxylat

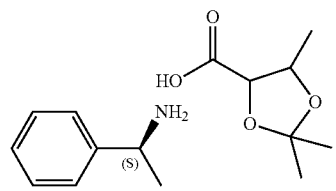

to a 72 L reaction bottle, then add a dilute phosphoric acid aqueous solution having a concentration of 10% to the system to regulate the pH at 1.5±0.5, control the temperature at −5±5° C., react for 1 hour, perform liquid separation to obtain an organic phase, add 3.7 kg of (0.8eq) N,N-diisopropylethylamine to the organic phase, and concentrate the system to obtain 5.3 kg of (4S,5S)-2,2,5-trimethyl-1,3-dioxolan-4-methanoic acid

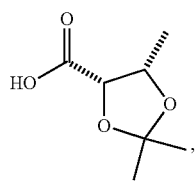

with a yield of 92.5%;

Step 5: add 42 L (8 ml/g) of 1,4-dioxane, 5.3 kg of 1,3-dioxolan-4-carboxylic acid

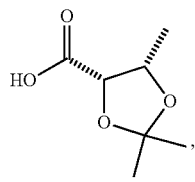

and 8.5 kg (2eq) of N,N-diisopropylethylamine to a 100 L reaction bottle, reduce the temperature to −10±5° C., add 4 kg (21.0eq) of propyl chloroformate, react for 2 hours while preserving the temperature, introduce a diazomethane gas for 2 hours, add 12 kg (2eq) of a hydrochloride ethanol solution having a concentration of 20%, react for 2 hours, add sodium hydroxide to regulate the pH value to 7.5±0.5, and perform extraction, liquid separation and concentration to obtain 5.1 kg of (4S,5S)-2,2,5-trimethyl-5-chloroacetyl-1,3-dioxolane

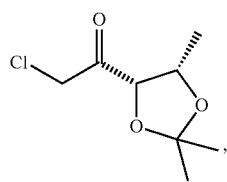

with a yield of 81%;

Step 6: add 41 L (8 ml/g) of tetrahydrofuran, 5.1 kg of (4S,5S)-2,2,5-trimethyl-5-chloroacetyl-1,3-dioxolane

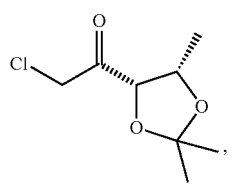

3.1 kg (1 eq) of azidotrimethylsilane, and 0.5 kg (0.1eq) of sodium iodide to a 72 L bottle, react the system for 30 hours while preserving the temperature at 12±5° C., perform filtering and concentration to obtain an acetone solution containing 4.6 kg of (4S,5S)-2,2,5-trimethyl-5-(2-azidoacetyl)-1,3-dioxolane

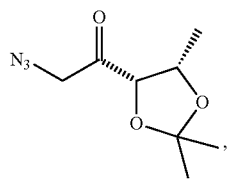

with a yield of 87.5%;

Step 7: add 28 L (6 ml/g) of 1,4-dioxane and 0.23 kg (0.05 g/g) of 10% palladium on carbon to a 50 L reaction kettle, introduce hydrogen until the system pressure is 0.8±0.1 MPa, regulate the pH of the system to 3±0.5 with acetic acid, add an acetonitrile solution containing 4.6 kg (1eq) of (4S,5S)-2,2,5-trimethyl-5-(2-azidoacetyl)-1,3-dioxolane

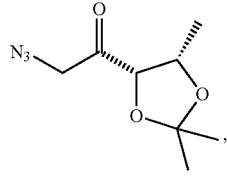

react at 27±5° C. for 8.5 hours, perform suction filtration and concentration to obtain 2.7 kg of (3S,4S)-1-amino-3,4-dihydroxy-2-pentanone

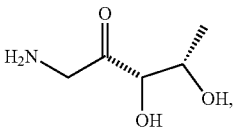

with a yield of 87.7%;

Step 8: add 16.3 L (6 ml/g) of isopropanol, 2.7 L (1 g/g) of pure water, 0.4 kg of (0.1eq) of sodium iodide, 4.8 kg (1.0eq) of compound A (2-amino-6-chloro-5-nitro-3H-pyrimidin-4-one), 2.7 kg (1eq) of (3S,4S)-1-amino-3,4-dihydroxy-2-pentanone

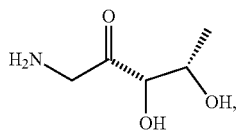

and 8.7 kg (4eq) of sodium carbonate to a 50 L reaction bottle, react the system for 7 hours while preserving the temperature at 45±5° C., then add an ammonium formate-ammonia aqueous solution to regulate the pH of the system to 6.5±0.5; and filter the system to obtain 2.85 kg of 2-acetylamino-5-nitro-6-((3S,4S)-3,3-dihydroxy-2-oxo-pentylamino)-pyrimidin-4-one

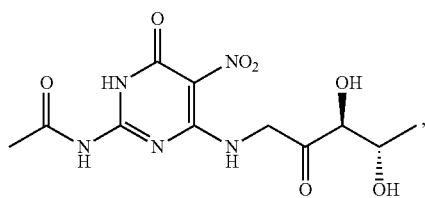 [SMILES: CC(=O)Nc1nc(NCC(=O)[C@@H](O)[C@H](C)O)c([N+](=O)[O-])c(=O)[nH]1]

with a yield of 42.5%;

Step 9: add 2 kg (1eq) of 2-acetylamino-5-nitro-6-((3S,4S)-3,3-dihydroxy-2-oxo-pentylamino)-pyrimidin-4-one

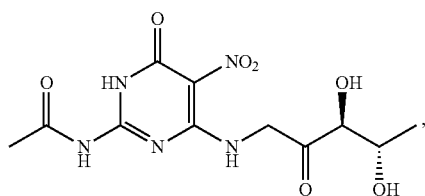 [SMILES: CC(=O)Nc1nc(NCC(=O)[C@@H](O)[C@H](C)O)c([N+](=O)[O-])c(=O)[nH]1]

60 L (30 ml/g) of ethanol and 0.2 kg (0.1 g/g) of platinum dioxide to a 100 L autoclave, introduce hydrogen until the reaction system pressure is 0.6±0.05 MPa, control the temperature of the system at 20±5° C. and the pressure at 0.6±0.05 MPa, react for 20 hours, filter the system, and regulate the pH to 11±0.5 to obtain an ethanol solution containing 1.7 kg of acetylamino-7,8-dihydropteridine

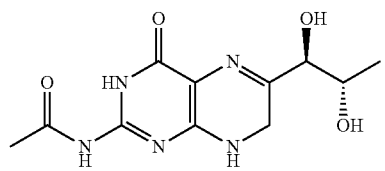 [SMILES: CC(=O)Nc1nc2c(c(=O)[nH]1)N=C([C@@H](O)[C@H](C)O)CN2]

which is used directly in the next step;

Step 10: add 0.2 kg (0.1 g/g) of platinum dioxide in the presence of the ethanol solution containing 1.7 kg of acetylamino-7,8-dihydropteridine

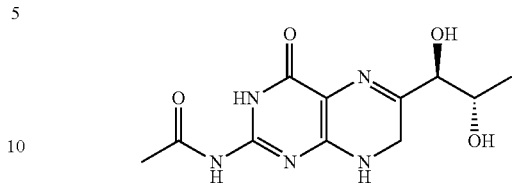

obtained in Step 9, introduce hydrogen until the pressure of the reaction kettle is 0.6±0.05 MPa, control the temperature of the system at 15±5° C. and the pressure at 0.6±0.05 MPa, react for 75 hours, after reacting thoroughly, perform quenching in 30 kg (5eq) of dilute hydrochloric acid having a concentration of 10%, and perform suction filtration and drying to the system to obtain a target product, i.e. a crude product of sapropterin dihydrochloride

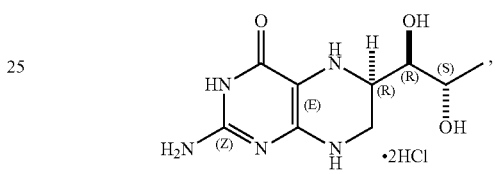

recrystallize and purify the crude product by 17 L (10 ml/g) of butanone at 15±5° C. to obtain 0.6 kg of a pure product, with a yield of 43%, a purity of 98.4% and an enantiomeric excess of 98.9%.

Thus, it can be seen that synthesis of a sapropterin dihydrochloride compound disclosed in a method of the present disclosure can obtain a target product with a high purity, a high enantiomeric excess, and a high yield. The synthesis method uses readily-available raw materials, significantly reduces a synthesis route of sapropterin dihydrochloride. The technological conditions are stable, and there is less pollution in the whole operation process, hence providing an effective scheme for mass industrial production of sapropterin dihydrochloride.

The above are only preferred embodiments of the present disclosure and should not be used to limit the present disclosure. For those skilled in the art, the present disclosure may have various modifications and changes. Any modifications, equivalent replacements, improvements and the like within the spirit and principle of the present disclosure shall fall within the scope of protection of the present disclosure.

What is claimed is:
1. A method for synthesizing sapropterin dihydrochloride, wherein it comprises the following specific steps:
Step 1: in the presence of a polar solvent, adding compound 1

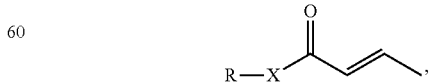

where X=NH or O, R=C1 to C6 alkyl or benzyl, increasing the system temperature to 35° C. to 50° C., adding an oxidant, reacting for 2 to 5 hours while maintaining the temperature, then adding a strong base aqueous solution having a concentration of 10% to 20% to the system, while maintaining the temperature, reacting the system for 3 to 4 hours after adding the strong base aqueous solution, and performing extraction and concentration to obtain compound 2 having the structural formula of

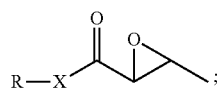

when X is NH, compound 1 is alkyl crotonamide, and compound 2 is 2,3 epoxy-alkylamide butyrate; when X is oxygen, compound 1 is alkyl crotonate or benzyl crotonate and compound 2 is 2,3 epoxy-alkylbutyrate or 2,3 epoxy-benzyl butyrate;

wherein concentration of the use amount of

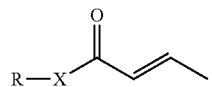

to that of the polar solvent is 1 g/5 to 20 ml, the molar ratio of

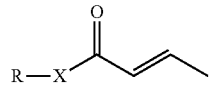

to the oxidant is 1:1 to 3, the molar ratio of

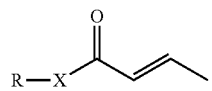

to the strong base is 1:1 to 3;

Step 2: adding a Lewis acid in the presence of acetone, controlling the temperature at 10° C. to 30° C., adding compound 2, reacting for 5 to 10 hours while maintaining the temperature, adding an inorganic base solution having a concentration of 5% to 10% to the system, and performing liquid separation, extraction and concentration to the system to obtain compound 3 having a structural formula of

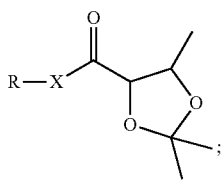

when X is NH, compound 3 is 2,3-acetonide-alkylbutyramide or 2,3-acetonide-benzylbutyramide; when X is oxygen, compound 3 is 2,3-acetonide-alkylbutyrate or 2,3-acetonide-benzyl butyrate;

wherein the molar ratio of compound 2 to acetone is 1:3 to 15; the molar ratio of compound 2 to the Lewis acid is 1:0.1 to 1; and the molar ratio of compound 2 to the inorganic base is 1:0.5 to 3;

Step 3: adding compound 3 in the presence of a polar solvent, increasing the temperature to 25° C. to 40° C., adding pure water and an alkaline solution, reacting for 3 to 8 hours while maintaining the temperature, performing centrifugation, dissolving a filter cake in a polar solvent which is the same as the polar solvent used in the reaction, adding a resolving reagent, maintaining the temperature at 15° C. to 30° C. for 3 to 5 hours, performing centrifugation and drying to obtain compound 4, i.e. 1-phenylalkylamine (4S,5S)-2,2,5-trimethyl-1,3-dioxolane-4-carboxylate having a structural formula of

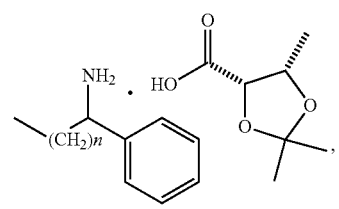

where n=0, 1;

wherein the concentration of the use amount of compound 3 to that of the polar solvent used in the reaction is 1 g/3 to 10 ml; the molar ratio of compound 3 to pure water is 1:0.5 to 3; the molar ratio of compound 3 to an alkaline substance in the alkaline solution is 1:0.5 to 2; the concentration of the use amount of compound 3 to that of the polar solvent for dissolving the filter cake is 1 g/2 to 10 ml; the molar ratio of compound 3 to the resolving reagent is 1:1 to 5;

Step 4: adding compound 4 in the presence of an ether solvent, then adding an inorganic acid aqueous solution having a concentration of 5% to 10% to the system to regulate the pH to 1 to 3, controlling the temperature at −10° C. to 10° C., performing liquid separation to obtain an organic phase, adding N,N-diisopropylethylamine to the organic phase, and concentrating the system to obtain compound 5, i.e. (4S,5S)-2,2,5-trimethyl-1,3-dioxolan-4-methanoic acid having a structural formula of

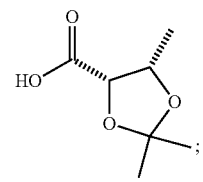

wherein the concentration of the use amount of compound 4 to that of the ether solvent is 1 g/3 to 10 ml and the molar ratio of compound 4 to N,N-diisopropylethylamine is 1:0.8 to 3;

Step 5: adding compound 5 and N,N-diisopropylethylamine in the presence of an ether solvent, reducing the temperature to −30° C. to 0° C., adding a chloroformate, reacting for 1 to 2 hours while maintaining the temperature, introducing a diazomethane gas for 1 to 2 hours, adding a hydrochloride ethanol solution, reacting for 1 to 2 hours, adding an alkaline reagent to regulate the pH value to 7 to 9, performing extraction, liquid separation and concentration to obtain compound 6, i.e. (4S,5S)-2,2,5-trimethyl-5-chloroacetyl-1,3-dioxolane having a structural formula of

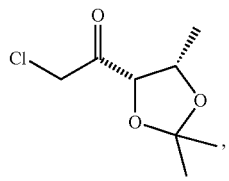

wherein the concentration of the use amount of compound 5 to that of the ether solvent is 1 g/5 to 15 ml; the molar ratio of compound 5 to N,N-diisopropylethylamine is 1:1 to 5; the molar ratio of compound 5 to the chloroformate is 1:1 to 3; and the molar ratio of compound 5 to hydrogen chloride in the hydrogen chloride-ethanol solution is 1:1 to 5;

Step 6: adding compound 6, a trinitride and a catalyst in the presence of a polar solvent, reacting the system at 15° C. to 40° C. for 20 to 30 hours while maintaining the temperature, then performing filtering and concentration to obtain a solution of compound 7 which is used directly in the next step; compound 7 is (4S,5S)-2,2,5-trimethyl-5-(2-azidoacetyl)-1,3-dioxolane having a structural formula of

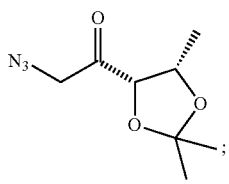

wherein the concentration of the use amount of compound 6 to that of the polar solvent is 1 g/5 to 15 ml; the molar ratio of compound 6 to the trinitride is 1:1 to 4; and the molar ratio of compound 6 to the catalyst is 1:0.05 to 0.8;

Step 7: adding triphenylphosphine and water, or palladium on carbon and hydrogen, or Raney nickel and hydrogen in the presence of an ether solvent, regulating the pH of the system to 1 to 4 with an acid reagent, adding a solution of compound 7, maintaining the temperature for 10° C. to 30° C., reacting for 5 to 10 hours, performing suction filtration and concentration to obtain a filtrate containing compound 8, the filtrate being used directly in the next step or a solid of compound 8 being separated from the filtrate for use in the next step; the compound 8 is (3S,4S)-1-amino-3,4-dihydroxy-2-pentanone having a structural formula of

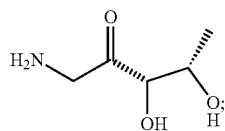

wherein the concentration of the use amount of compound 7 to that of the ether solvent is 1 g/5 to 15 ml; the molar ratio of compound 7 to triphenylphosphine is 1:0.1 to 3; the ratio of the use amount of compound 7 to that of water is 1:0.1 to 3; the mass ratio of compound 7 to 5% palladium on carbon or 10% palladium on carbon or Raney nickel is 1:0.05 to 0.6; the hydrogen is introduced until the pressure of the system is 0.4 to 0.9 MPa;

Step 8: adding a catalyst, compound A, i.e. 2-amino-6-chloro-5-nitro-3H-pyrimidin-4-one having a structural formula of

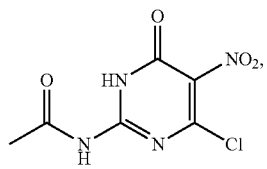

compound 8, and an alkaline reagent in the presence of an alcoholic solvent and pure water, reacting the system at 30° C. to 80° C. for 4 to 8 hours while maintaining the temperature, adding a buffer solution to regulate the pH of the system to 6 to 8, and filtering the system to obtain compound 9, i.e. 2-acetylamino-5-nitro-6-((3S,4S)-3,3-dihydroxy-2-oxo-pentylamino)-pyrimidin-4-one having a structural formula of

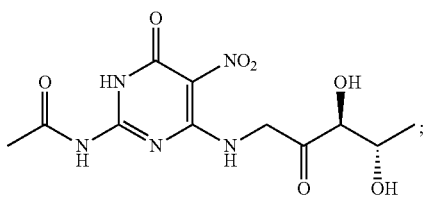 [SMILES: CC(=O)Nc1nc(NCC(=O)[C@@H](O)[C@H](C)O)c([N+](=O)[O-])c(=O)[nH]1]

wherein the concentration of the use amount of compound 8 to that of the alcoholic solvent is 1 g/5 to 15 ml; the concentration of the use amount of compound 8 to that of pure water is 1 g/1 to 5 ml; the molar ratio of compound 8 to compound A is 1:1 to 1.5; the molar ratio of compound 8 to the catalyst is 1:0.05 to 0.5; and the molar ratio of compound 8 to the alkaline reagent is 1:3 to 8;

Step 9: adding a catalyst in the presence of compound 9 and a polar solvent, introducing hydrogen until the pressure of the system is 0.4 to 0.9 MPa, controlling the temperature of the system at 15° C. to 30° C. and the pressure at 0.4 to 0.9 MPa, reacting for 18 to 24 hours, filtering the system, and regulating the pH of the system to 11 to 12 with an alkaline reagent to obtain a solution of compound 10 to be used directly in the next step, compound 10 is acetylamino-7,8-dihydropteridine having a structural formula of

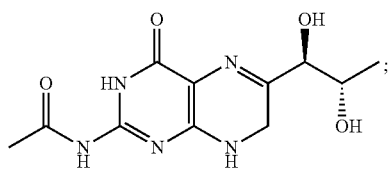 [SMILES: CC(=O)Nc1nc2c(c(=O)[nH]1)N=C([C@@H](O)[C@H](C)O)CN2]

wherein the concentration of the use amount of compound 9 to that of the polar solvent is 1 g/20 to 50 ml and the mass ratio of compound 9 to the catalyst is 1:0.05 to 0.6;

Step 10: adding a catalyst in the presence of the solution of the compound 10 obtained in Step 9, introducing hydrogen until the pressure of the system is 0.4 to 0.9 MPa, controlling the temperature of the system at 10° C. to 30° C., controlling the pressure at 0.4 to 0.9 MPa, reacting for 72 to 84 hours, performing quenching in dilute hydrochloric acid having a concentration of 10% to 20% after reacting thoroughly, and performing suction filtration and drying to the system to obtain compound 11, i.e. a target product, a sapropterin dihydrochloride crude product, and further crystallizing and purifying the sapropterin dihydrochloride crude product with an alcoholic solvent or a ketone solvent at 0° C. to 40° C. to obtain a sapropterin dihydrochloride pure product, wherein the mass ratio of compound 10 to the catalyst is 1:0.05 to 0.6; the molar ratio of compound 10 to hydrochloric acid is 1:3 to 10; and the concentration of the use amount of compound 10 to that of the alcoholic solvent or the ketone solvent is 1 g/5 to 25 ml.

2. A method for synthesizing sapropterin dihydrochloride according to claim 1, wherein in Step 1 polar solvent is water, methanol, ethanol or isopropanol; the oxidant is N-bromobutanimide, meta-chloroperoxybenzoic acid, hydrogen peroxide having a concentration of 35% or a toluene solution of tert-butyl hydroperoxide having a concentration of 50%; the strong base is sodium hydroxide or potassium hydroxide; the concentration of the use amount of

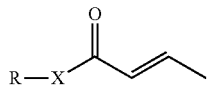

to that of the polar solvent is 1 g/5 to 15 ml; the molar ratio of

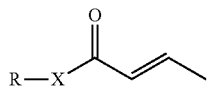

to the oxidant is 1:1 to 2.5; the molar ratio of

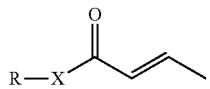

to the strong base is 1:1 to 2.5.

3. A method for synthesizing sapropterin dihydrochloride according to claim 1, wherein in Step 2, the Lewis acid is aluminium chloride, ferric chloride, zinc chloride, a boron trifluoride diethyl etherate solution having a concentration of 47%, zinc bromide, or lithium chloride; the inorganic base is sodium bicarbonate, sodium carbonate, sodium hydroxide, potassium hydroxide, potassium carbonate or potassium bicarbonate; the ratio of the use amount of compound 2 to that of acetone is 1:5 to 15; the molar ratio of compound 2 to the Lewis acid is 1:0.1 to 0.8; the ratio of the use amount of compound 2 to that of the inorganic base is 1:0.5 to 2.5.

4. A method for synthesizing sapropterin dihydrochloride according to claim 1, wherein in Step 3, the polar solvent is tetrahydrofuran, methanol or ethanol; the resolving reagent is L-α-phenylethylamine or L-α-amphetamine; the alkaline solution is a methanol solution of sodium methoxide having a concentration of 29%, a potassium hydroxide aqueous solution having a concentration of 20% or a sodium hydroxide aqueous solution having a concentration of 20%; the concentration of the use amount of compound 3 to that of the polar solvent is 1 g/3 to 8 ml; the molar ratio of compound 3 to pure water is 1:0.5 to 1.8; the molar ratio of compound 3 to the alkaline substance in the alkaline solution is 1:0.5 to 1.8; the concentration of the use amount of compound 3 to that of the polar solvent for dissolving the filter cake is 1 g/3 to 8 ml; the molar ratio of compound 3 to the resolving reagent is 1:1 to 4.

5. A method for synthesizing sapropterin dihydrochloride according to claim 1, wherein in Step 4, the ether solvent is tetrahydrofuran, 2-methyltetrahydrofuran, methyl tert-butyl ether, 1,4-dioxane or ether; the inorganic acid is sulphuric acid, hydrochloric acid or phosphoric acid; the concentration of the use amount of compound 4 to that of the ether solvent is 1 g/3 to 8 ml; and the molar ratio of compound 4 to N,N-diisopropylethylamine is 1:0.8 to 2.5.

6. A method for synthesizing sapropterin dihydrochloride according to claim 1, wherein in Step 5, the ether solvent is tetrahydrofuran, 2-methyltetrahydrofuran, methyl tert-butyl ether, 1,4-dioxane or ether; the chloroformate is methyl chloroformate, ethyl chloroformate, or propyl chloroformate; the alkaline reagent is triethylamine, sodium carbonate, potassium carbonate, sodium bicarbonate, potassium bicarbonate, sodium hydroxide or potassium hydroxide; the concentration of the use amount of compound 5 to that of the ether solvent is 1 g/6 to 12 ml; the molar ratio of compound 5 to N,N-diisopropylethylamine is 1:1.5 to 4; the molar ratio of compound 5 to the chloroformate is 1:1 to 2.5; and the molar ratio of compound 5 to hydrogen chloride is 1:1.5 to 4.5.

7. A method for synthesizing sapropterin dihydrochloride according to claim 1, wherein in Step 6, the polar solvent is acetonitrile, methanol, ethanol, acetone or tetrahydrofuran; the catalyst is sodium iodide or potassium iodide; the trinitride is sodium azide or azidotrimethylsilane; the concentration of the use amount of compound 6 to that of the polar solvent is 1 g/6 to 12 ml; the molar ratio of compound 6 to the trinitride is 1:1 to 3; and the molar ratio of compound 6 to the catalyst is 1:0.05 to 0.6.

8. A method for synthesizing sapropterin dihydrochloride according to claim 1, wherein in Step 7, the ether solvent is tetrahydrofuran, 2-methyltetrahydrofuran, methyl tert-butyl ether, 1,4-dioxane or ether; the acid reagent is citric acid, p-toluenesulfonic acid, benzenesulfonic acid, formic acid, acetic acid, hydrochloric acid, sulfuric acid or phosphoric acid; the concentration of the use amount of compound 7 to that of the ether solvent is 1 g/5 to 12 ml.

9. A method for synthesizing sapropterin dihydrochloride according to claim 1, wherein in Step 8, the alcoholic solvent is methanol, ethanol, propanol or isopropanol; the catalyst is sodium iodide or potassium iodide; the alkaline reagent is triethylamine, diisopropylethylamine, diisopropylamine, pyridine, sodium bicarbonate, potassium bicarbonate, sodium carbonate, potassium carbonate or cesium carbonate; the buffer solution is a sodium dihydrogen phosphate-disodium hydrogen phosphate aqueous solution, a potassium dihydrogen phosphate-dipotassium hydrogen phosphate aqueous solution or an ammonium formate-ammonia aqueous solution; the concentration of the use amount of compound 8 to that of the alcoholic solvent is 1 g/6 to 12 ml; the concentration of the use amount of compound 8 to that of pure water is 1 g/1 to 4 ml; the molar ratio of compound 8 to compound A is 1:1 to 1.4; the molar ratio of compound 8 to the catalyst is 1:0.1 to 0.4; and the molar ratio of compound 8 to the alkaline reagent is 1:4 to 7;

in Step 9, the catalyst is Raney nickel, 5% palladium on carbon, 10% palladium on carbon, platinum dioxide or 20% palladium on carbon; the polar solvent is pure water, methanol or ethanol; the alkaline solution is sodium hydroxide, potassium hydroxide, sodium carbonate or potassium carbonate; the concentration of the use amount of compound 9 to that of the polar solvent is 1 g/25 to 45 ml and the mass ratio of compound 9 to the catalyst is 1:0.05 to 0.5 in Step 10, the catalyst is Raney nickel, 5% palladium on carbon, 10% palladium on carbon, platinum dioxide or 20% palladium on carbon; the alcoholic solvent is methanol, ethanol, isopropanol or n-butanol; the ketone solvent is acetone or butanone; the mass ratio of compound 10 to the catalyst is 1:0.05 to 0.5; the molar ratio of compound 10 to hydrochloric acid is 1:4 to 9; and the concentration of the use amount of compound 10 to that of the alcoholic solvent or the ketone solvent is 1 g/5 to 20 ml.

* * * * *